US011950952B2

(12) United States Patent
Kim et al.

(10) Patent No.: US 11,950,952 B2
(45) Date of Patent: Apr. 9, 2024

(54) MOBILE X-RAY DETECTOR, X-RAY IMAGING APPARATUS INCLUDING MOBILE X-RAY DETECTOR, AND OPERATING METHOD OF MOBILE X-RAY DETECTOR AND X-RAY IMAGING APPARATUS

(71) Applicant: SAMSUNG ELECTRONICS CO., LTD., Suwon-si (KR)

(72) Inventors: Uncheol Kim, Suwon-si (KR); Sungwoo Lee, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 18/076,642

(22) Filed: Dec. 7, 2022

(65) Prior Publication Data

US 2023/0104097 A1 Apr. 6, 2023

Related U.S. Application Data

(63) Continuation of application No. 17/091,933, filed on Nov. 6, 2020, now Pat. No. 11,540,802.

(30) Foreign Application Priority Data

Nov. 8, 2019 (KR) .................. 10-2019-0142998

(51) Int. Cl.
*A61B 6/00* (2006.01)
*A61B 6/46* (2024.01)
(52) U.S. Cl.
CPC .............. *A61B 6/56* (2013.01); *A61B 6/4405* (2013.01); *A61B 6/461* (2013.01); *A61B 6/467* (2013.01); *A61B 6/5205* (2013.01)

(58) Field of Classification Search
CPC ... A61B 6/4283; A61B 6/4266; A61B 6/4494; A61B 6/463; A61B 6/467; A61B 6/4405;
(Continued)

(56) References Cited

U.S. PATENT DOCUMENTS 7,985,955 B2 7/2011 Ohta et al.
11,540,802 B2 * 1/2023 Kim ................ A61B 6/563
(Continued)

FOREIGN PATENT DOCUMENTS

CN 101146481 A 3/2008
JP 2006250727 A 9/2006
(Continued)

OTHER PUBLICATIONS

US 10,070,832 B2, 09/2018, SHimizukawa et al. (withdrawn)
(Continued)

*Primary Examiner* — Don K Wong
(74) *Attorney, Agent, or Firm* — Sughrue Mion, PLLC

(57) ABSTRACT

A method, performed by a mobile X-ray detector, of processing an X-ray image, including generating the X-ray image of an object by detecting an X-ray transmitted through the object and converting the detected X-ray into an electrical signal; detecting a power supply stoppage which prevents transmission of the generated X-ray image from the mobile X-ray detector to a workstation; based on the detecting of the power supply stoppage, storing the X-ray image in a nonvolatile memory inside the mobile X-ray detector; and after storing the X-ray image, deactivating the mobile X-ray detector.

20 Claims, 21 Drawing Sheets

(58) Field of Classification Search
CPC ....... A61B 6/461; A61B 6/563; A61B 6/4452; A61B 6/465; A61B 6/54; A61B 6/566; A61B 6/5205; A61B 6/548
See application file for complete search history.

(56) References Cited

U.S. PATENT DOCUMENTS

2006/0054829 A1    3/2006  Tsuchino et al.
2016/0078596 A1*   3/2016  Ohashi .................. A61B 6/566
                                                      378/62

FOREIGN PATENT DOCUMENTS

| JP | 2010137058 A | 6/2010 | |
|---|---|---|---|
| JP | 2018-89438 A | 6/2018 | |
| JP | 201894307 A | 6/2018 | |
| KR | 10-0863299 B1 | 10/2008 | |
| KR | 20210056181 A * | 5/2021 | ............... G01T 7/02 |

OTHER PUBLICATIONS

Communication dated Feb. 22, 2023 by the European Patent Office in counterpart European Patent Application No. 20206227.9.
Communication dated Apr. 13, 2021 issued by the European Patent Office in application No. 20206227.9.

* cited by examiner

MOBILE X-RAY DETECTOR, X-RAY IMAGING APPARATUS INCLUDING MOBILE X-RAY DETECTOR, AND OPERATING METHOD OF MOBILE X-RAY DETECTOR AND X-RAY IMAGING APPARATUS

CROSS-REFERENCE TO RELATED APPLICATION

This is a Continuation of U.S. application Ser. No. 17/091,933 filed Nov. 6, 2020, which is based on and claims priority under 35 U.S.C. § 119 to Korean Patent Application No. 10-2019-0142998, filed on Nov. 8, 2019, in the Korean Intellectual Property Office, the disclosure of which is incorporated by reference herein in its entirety.

BACKGROUND

1. Field

The disclosure relates to a mobile X-ray detector, an X-ray imaging apparatus including the mobile X-ray detector, and an operating method of the mobile X-ray detector and the X-ray imaging apparatus. More particularly, the disclosure relates to a mobile X-ray detector that processes an X-ray image when an exceptional situation occurs in which the X-ray image generated by the mobile X-ray detector is unable to be transmitted to a workstation.

2. Description of Related Art

X-rays are electromagnetic waves having wavelengths of 0.01 to 100 angstroms (Å), and may be widely used, due to their ability to penetrate objects, in medical apparatuses for imaging the inside of a living body or in non-destructive testing equipment for industrial use.

A basic principle of an X-ray imaging apparatus using X-rays is that an internal structure of an object may be examined by transmitting X-rays emitted from an X-ray tube, or an X-ray source, through the object and detecting a difference in intensities of the transmitted X-rays via an X-ray detector.

Recently, a wireless X-ray detector including a battery and a wireless communicator for wirelessly transmitting/receiving X-ray image data to/from an external device such as a workstation has been used. A wireless X-ray detector may be easy to carry, may have few restrictions with respect to an imaging space, and may improve user convenience, and thus is widely used. An X-ray image generated by a wireless X-ray detector may be stored in an internal memory, and a volatile memory having a high write speed and having no upper limit on the number of updates may be used as the internal memory. However, when there occurs an exceptional situation where an X-ray image is unable to be transmitted to a workstation, for example, when a battery of a mobile X-ray detector has no remaining amount, the battery is separated, or power is forcibly turned off due to an external input, power supply to a volatile memory may be cut off and thus image information may be lost. Once X-ray image data generated by the mobile X-ray detector is lost, re-imaging may be needed, which may include unnecessarily re-emitting an X-ray to a patient's body, thereby leading to excessive X-ray emission exposure.

SUMMARY

Provided are a mobile X-ray detector for processing an X-ray image in an exceptional situation in which the X-ray image is unable to be transmitted to a workstation, and an operating method of the mobile X-ray detector.

Provided are an X-ray imaging apparatus for processing an X-ray image that is not transmitted, or whose transmission is stopped, from among X-ray images obtained by a mobile X-ray detector, and an operating method of the X-ray imaging apparatus.

Additional aspects will be set forth in part in the description which follows and, in part, will be apparent from the description, or may be learned by practice of the presented embodiments of the disclosure.

According to an embodiment of the disclosure, a method, performed by a mobile X-ray detector, of processing an X-ray image, includes generating the X-ray image of an object by detecting an X-ray transmitted through the object and converting the detected X-ray into an electrical signal; detecting a power supply stoppage which prevents transmission of the generated X-ray image from the mobile X-ray detector to a workstation; based on the detecting of the power supply stoppage, storing the X-ray image in a nonvolatile memory inside the mobile X-ray detector; and after storing the X-ray image, deactivating the mobile X-ray detector.

The method may further include determining that the storing of the X-ray image in the nonvolatile memory is completed, and the mobile X-ray detector may be deactivated after the storing of the X-ray image is determined to be completed.

The power supply stoppage may occur based on a user input of pressing a power button disposed on a side portion of the mobile X-ray detector and exposed to an outside of the mobile X-ray detector, and the deactivating the mobile X-ray detector may include counting an amount of time for which the power button is pressed; and based on the counted amount of time being greater than a predetermined amount of time, deactivating the mobile X-ray detector.

The detecting of the power supply stoppage may include detecting a removal of a main battery mounted on the mobile X-ray detector, and the method may further include supplying power to the mobile X-ray detector through an auxiliary power supplier located inside the mobile X-ray detector for a predetermined time after detecting the removal of the main battery.

The predetermined time may start when power is supplied to the mobile X-ray detector using power pre-stored in the auxiliary power supplier, and may end when the pre-stored power is exhausted, and the X-ray image may be stored in the nonvolatile memory during the predetermined time.

The method may further include detecting whether an external memory card is inserted into a socket of the mobile X-ray detector; and identifying state information comprising at least one of a type of the external memory card, compatibility information, capacity information, or information about whether a write operation is possible, and the storing of the X-ray image in the nonvolatile memory may include storing the X-ray image in the external memory card based on the state information.

The method may further include after the mobile X-ray detector is deactivated, detecting a power supply activation; and after the power supply activation is detected, reactivating the mobile X-ray detector and transmitting the X-ray image stored in the nonvolatile memory to the workstation.

According to an embodiment of the disclosure, a mobile X-ray detector for processing an X-ray image, includes an X-ray receiver configured to detect an X-ray transmitted through an object and convert the detected X-ray into an electrical signal; a communicator configured to perform data communication with a workstation; a memory configured to store instructions for processing the X-ray image; a processor configured to execute the instructions stored in the memory; and a power supplier configured to supply power to the X-ray receiver, the processor, the memory, and the communicator, wherein the processor is configured to: generate the X-ray image of the object by using the electrical signal, detect a power supply stoppage which prevents transmission of the X-ray image to the workstation, based on the detecting of the power supply stoppage, store the X-ray image in a nonvolatile memory, and deactivate the mobile X-ray detector after the X-ray image is stored.

The processor may be further configured to determine that the storing of the X-ray image in the nonvolatile memory is completed, and then control the power supplier to deactivate the mobile X-ray detector.

The mobile X-ray detector may further include a power button disposed on a side portion of the mobile X-ray detector and exposed to an outside of the mobile X-ray detector, the power supply stoppage may occur due to a user input of pressing the power button, and the processor may be further configured to count an amount of time for which the power button is pressed, and when the counted amount of time is greater than a predetermined threshold amount of time, deactivate the mobile X-ray detector.

The power supplier may include a main battery detachably mounted on the mobile X-ray detector and an auxiliary power supplier located inside the mobile X-ray detector, and the processor may be further configured to detect a removal of the main battery and to control the auxiliary power supplier to supply power to the X-ray receiver, the processor, the memory, and the communicator for a predetermined time after detecting the removal of the main battery.

The predetermined time may start when power is supplied to the mobile X-ray detector using power pre-stored in the auxiliary power supplier, and may end when the pre-stored power is exhausted, and the processor may be further configured to store the X-ray image in the nonvolatile memory during the predetermined time.

The memory may include an external memory card inserted into a socket of the mobile X-ray detector and capable of storing data, and the processor may be further configured to: detect whether the external memory card is inserted into the socket, identify state information comprising at least one of a type of the external memory card, compatibility information, capacity information, or information about whether a write operation is possible, and store the X-ray image in the external memory card based on the state information.

The processor may be further configured to detect a power supply activation after the mobile X-ray detector is deactivated, and to reactivate the mobile X-ray detector and control the communicator to transmit the X-ray image stored in the nonvolatile memory to the workstation after the power supply activation is detected.

According to an embodiment of the disclosure, an operating method of an X-ray apparatus including a mobile X-ray detector and a workstation includes displaying, by the workstation, on a display of the workstation, at least one user interface (UI) indicating imaging information of at least one non-transmitted X-ray image from among X-ray images generated by the mobile X-ray detector; receiving, by the workstation, a user input selecting a UI of the displayed at least one UI; transmitting, by the workstation, to the mobile X-ray detector, imaging information of an X-ray image corresponding to the selected UI and a request signal for requesting transmission the X-ray image; identifying, by the mobile X-ray detector, the X-ray image based on the received imaging information from among the at least one non-transmitted X-ray image stored in a nonvolatile memory, in response to the request signal; transmitting, by the mobile X-ray detector, the identified X-ray image to the workstation; and displaying, by the workstation, the X-ray image transmitted by the mobile X-ray detector on the display.

The imaging information may include patient identification information and imaging protocol information of the at least one non-transmitted X-ray image.

According to an embodiment of the disclosure, an operating method of an X-ray imaging apparatus including a mobile X-ray detector and a workstation includes transmitting, by the mobile X-ray detector, to the workstation, imaging information of a plurality of X-ray images generated by the mobile X-ray detector and information about transmission of the plurality of X-ray images; upon receiving the imaging information of the plurality of X-ray images and the information about the transmission of the plurality of X-ray images, transmitting, by the workstation, a request signal for requesting a plurality of thumbnail images corresponding to the plurality of X-ray images to the mobile X-ray detector; generating, by the mobile X-ray detector, the plurality of thumbnail images corresponding to the plurality of X-ray images in response to the request signal, and transmitting the generated plurality of thumbnail images to the workstation; displaying, by the workstation, the plurality of thumbnail images received from the mobile X-ray detector on a display; receiving, by the workstation, a user input selecting a thumbnail image of the displayed plurality of thumbnail images; transmitting, by the workstation, a request signal for requesting to transmit an X-ray image corresponding to the thumbnail image selected based on the user input to the mobile X-ray detector; and transmitting, by the mobile X-ray detector, the X-ray image to the workstation.

The operating method may further include: detecting, by the workstation, a non-transmitted X-ray image; and displaying a user interface (UI) for requesting transmission of the non-transmitted X-ray image on the display, and the transmitting of the imaging information of the plurality of X-ray images and the information about the transmission of the plurality of X-ray images to the workstation may be performed in response to a user input selecting the UI.

According to an embodiment of the disclosure, an X-ray imaging apparatus includes a mobile X-ray detector; and a workstation, wherein the workstation includes a display; a user input interface; a communicator configured to perform data communication with the mobile X-ray detector; and a controller, wherein the controller is configured to: control the display to display at least one user interface (UI) indicating imaging information of at least one non-transmitted X-ray image from among X-ray images generated by the mobile X-ray detector, control the user input interface to receive a user input selecting a UI of the at least one UI, and control the communicator to transmit, to the mobile X-ray detector, imaging information of an X-ray image corresponding to the selected UI and a request signal for requesting transmission of the X-ray image, wherein the mobile X-ray detector is configured to identify the X-ray image based on the received imaging information from among the at least one non-transmitted X-ray image stored in a non-volatile memory based on the request signal received from the workstation, and to transmit the identified X-ray image to the workstation, and wherein the controller may be further configured to control the display to display the X-ray image obtained from the mobile X-ray detector on the display.

The imaging information may include patient identification information and imaging protocol information of the at least one non-transmitted X-ray image.

According to an embodiment of the disclosure, an X-ray imaging apparatus includes a mobile X-ray detector; and a workstation, wherein the workstation includes: a display; a user input interface; a communicator configured to perform data communication with the mobile X-ray detector; and a controller, wherein the controller is configured to: control the communicator to receive, from the mobile X-ray detector, imaging information of a plurality of X-ray images generated by the mobile X-ray detector and information about transmission of the plurality of X-ray images, after receiving the imaging information of the plurality of X-ray images and the information about the transmission of the plurality of X-ray images, transmit a request signal for requesting a plurality of thumbnail images of the plurality of X-ray images to the mobile X-ray detector, and receive the plurality of thumbnail images from the mobile X-ray detector, control the display to display the plurality of thumbnail images on the display, and control the communicator to receive a user input selecting a thumbnail image of the displayed plurality of thumbnail images through the user input interface and transmit, to the mobile X-ray detector, a request signal for requesting transmission of an X-ray image corresponding to the selected thumbnail image, and wherein the mobile X-ray detector is configured to: generate the plurality of thumbnail images corresponding to the plurality of X-ray images in response to the request signal, transmit the generated plurality of thumbnail images to the workstation, and transmit the X-ray image to the workstation.

The controller may be further configured to detect a non-transmitted X-ray image and to control the display to display, on the display, a user interface (UI) for requesting transmission of the non-transmitted X-ray image.

The controller may be further configured to receive a user input selecting the UI through the user input interface, and to transmit, to the mobile X-ray detector, a request signal requesting transmission of the imaging information of the plurality of X-ray images and the information about the transmission of the plurality of X-ray images based on the received user input, and the mobile X-ray detector may be further configured to transmit the imaging information of the plurality of X-ray images and the information about the transmission of the plurality of X-ray images to the workstation based on the request signal.

According to an embodiment of the disclosure, a computer-readable recording medium may have embodied thereon at least one program for executing the methods disclosed herein.

BRIEF DESCRIPTION OF THE DRAWINGS

The above and other aspects, features, and advantages of certain embodiments of the disclosure will be more apparent from the following description taken in conjunction with the accompanying drawings, in which.

DETAILED DESCRIPTION

Figure 1:
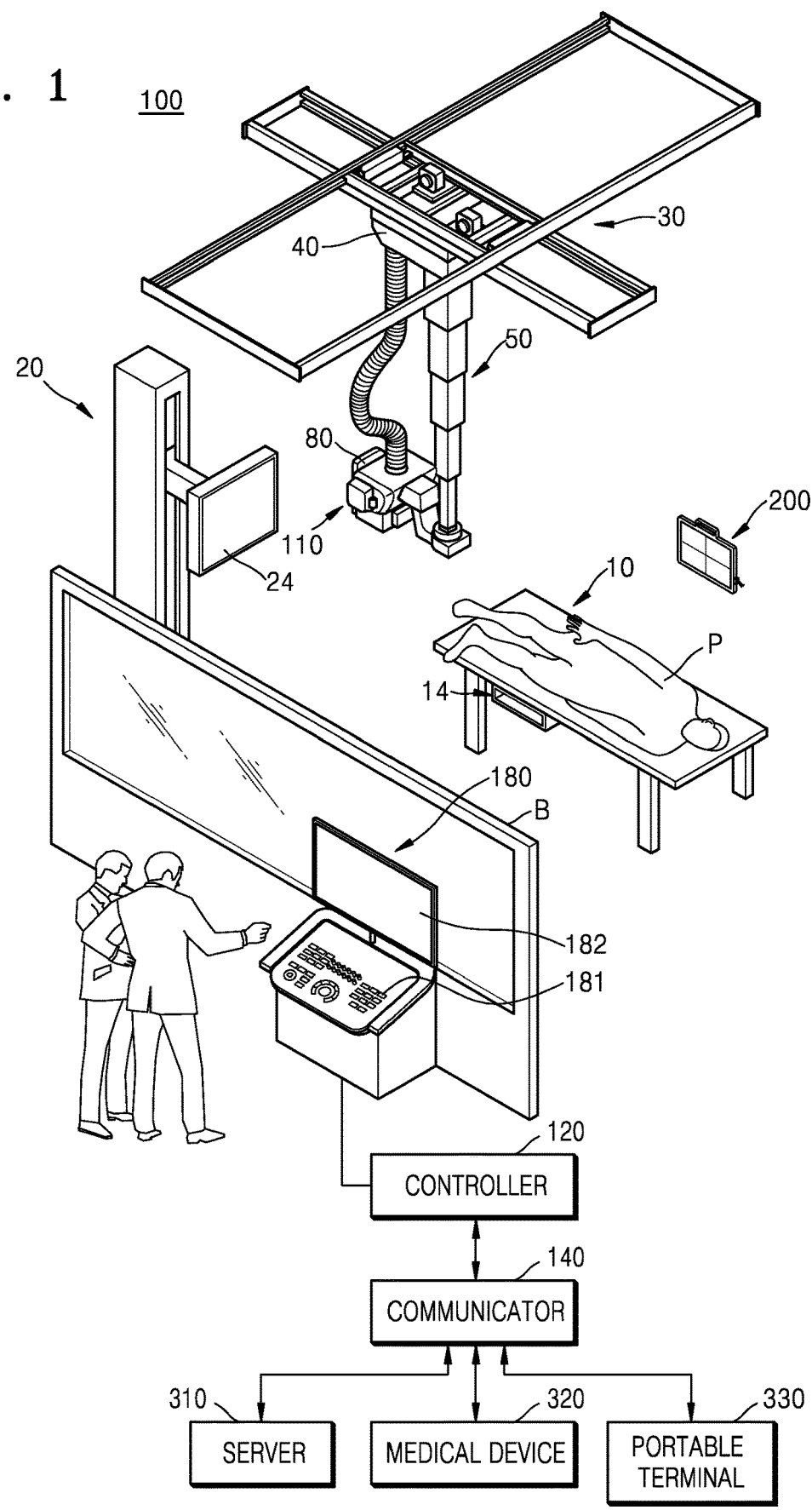
FIG. 1 is an exterior view illustrating a configuration of an X-ray imaging apparatus according to an embodiment.

Certain embodiments of the disclosure are described in greater detail below with reference to the accompanying drawings.

In the following description, the same drawing reference numerals may be used for the same elements even in different drawings. The matters defined in the description, such as detailed construction and elements, are provided to assist in a comprehensive understanding of embodiments of the disclosure. Thus, it is apparent that embodiments of the disclosure may be carried out without those specifically defined matters. Also, well-known functions or constructions may not described in detail because they would obscure embodiments of the disclosure with unnecessary detail.

Terms such as "part" and "portion" used herein denote those that may be embodied by software or hardware. According to embodiments of the disclosure, a plurality of parts or portions may be embodied by a single unit or element, or a single part or portion may include a plurality of elements.

Throughout the disclosure, the expression "at least one of a, b or c" may indicate only a, only b, only c, both a and b, both a and c, both b and c, all of a, b, and c, or variations thereof.

In the present disclosure, an "object" may be a target to be imaged and may include a human, an animal, or a part of a human or animal. For example, the object may include a body part (an organ, tissue, etc.) or a phantom.

FIG. 1 is an exterior diagram illustrating a configuration of an X-ray imaging apparatus 100 according to an embodiment of the disclosure. FIG. 1 will be described assuming that the X-ray imaging apparatus 100 is a fixed X-ray imaging apparatus.

Referring to FIG. 1, the X-ray imaging apparatus 100 may include an X-ray emitter 110 for generating and emitting an X-ray, an X-ray detector 200 for detecting an X-ray emitted from the X-ray emitter 110 and transmitted through an object, and a workstation 180 for receiving a command from a user and providing information to the user. Also, the X-ray imaging apparatus 100 may include a controller 120 for controlling the X-ray imaging apparatus 100 according to the command and a communicator 140 for communicating with an external device.

Some or all of the components of the controller 120 and the communicator 140 may be included in the workstation 180 or provided separately from the workstation 180.

The X-ray emitter 110 may include an X-ray source for generating an X-ray and a collimator for adjusting an emission area of the X-ray generated by the X-ray source.

A guide rail 30 may be installed on the ceiling of an examination room where the X-ray imaging apparatus 100 is located, the X-ray emitter 110 may be moved to a location corresponding to a location of a target object P by connecting the X-ray emitter 110 to a moving carriage 40 moving along the guide rail 30, and the moving carriage 40 and the X-ray emitter 110 may be connected to each other through a foldable post frame 50 to adjust a height of the X-ray emitter 110.

The workstation 180 may include an input interface 181 for receiving commands from the user and a display 182 for displaying information.

The input interface 181 may receive commands for controlling an imaging protocol, imaging conditions, an imaging timing, a position of the X-ray emitter 110, etc. The input interface 181 may include a keyboard, a mouse, a touchscreen, a voice recognizer, etc.

The display 182 may display a screen image for guiding an input of a user, an X-ray image, a screen image showing a state of the X-ray imaging apparatus 100, etc.

The controller 120 may control the imaging timing and the imaging conditions of the X-ray emitter 110 according to the command input from the user and may generate a medical image by using image data received from the X-ray detector 200. Furthermore, the controller 120 may control positions or postures of mount portions 14 and 24 on which the X-ray emitter 110 or the X-ray detector 200 is mounted according to the imaging protocol and a position of the target object P.

The controller 120 may include a memory for storing a program for performing the above-described operation and other operations and a processor for executing the stored program. The controller 120 may include a single processor or a plurality of processors, and in the latter case, the plurality of processors may be integrated on a single chip or may be physically separated from one another.

The X-ray imaging apparatus 100 may be connected to an external device, for example an external server 310, a medical device 320, or a portable terminal 330, for example a smart phone, a tablet personal computer (PC), or a wearable device, via the communicator 140 and may transmit or receive data.

The communicator 140 may include at least one component for communication with an external device. For example, the communicator 140 may include at least one of a short-range communication module, a wired communication module, or a wireless communication module.

Furthermore, the communicator 140 may receive a control signal from an external device, and may transmit the received control signal to the controller 120 so that the controller 120 controls the X-ray imaging apparatus 100 according to the received control signal.

Furthermore, the controller 120 may control an external device according to a control signal of the controller 120 by transmitting the control signal to the external device through the communicator 140. For example, the external device may process data of the external device according to the control signal of the controller 120 received via the communicator 140.

Furthermore, the communicator 140 may further include an internal communication module for communication among the components of the X-ray imaging apparatus 100. Because a program for controlling the X-ray imaging apparatus 100 may be installed on the external device, the program may include an instruction for performing some or all of operations of the controller 120.

The program may be installed in the portable terminal 330 in advance or the user of the portable terminal 330 may download the program from a server that provides applications and may install the program. The server providing the applications may include a recording medium in which the program is stored.

The X-ray detector 200 may be a fixed X-ray detector fixed to a stand 20 or a table 10, may be detachably mounted to the mount portions 14 and 24, or may be a portable X-ray detector that may be used at an arbitrary location. When the X-ray detector 200 is a portable X-ray detector, the X-ray detector 200 may be of a wire type or a wireless type depending on a data transmission method and a power supply method.

The X-ray detector 200 may be included as an element of the X-ray imaging apparatus 100 or may not be included. In the latter case, the X-ray detector 200 may be registered in the X-ray imaging apparatus 100 by the user. Furthermore, in both cases, the X-ray detector 200 may be connected to the controller 120 through the communicator 140 and receive a control signal or transmit image data.

A sub-user interface 80 for providing information to the user and receiving a command from the user may be provided on a side surface of the X-ray emitter 110, and some or all of functions performed by the input interface 181 and the display 182 of the workstation 180 may be performed by the sub-user interface 80.

When all or some of the components of the controller 120 and the communicator 140 are provided separately from the workstation 180, the components may be included in the sub-user interface 80 provided on the X-ray emitter 110.

Although FIG. 1 shows a fixed X-ray imaging apparatus connected to the ceiling of an examination room, the X-ray imaging apparatus 100 may be an X-ray imaging apparatus having any of various structures within a range that is obvious to one of ordinary skill in the art, such as a C-arm type X-ray apparatus or a mobile X-ray apparatus.

Figure 2:
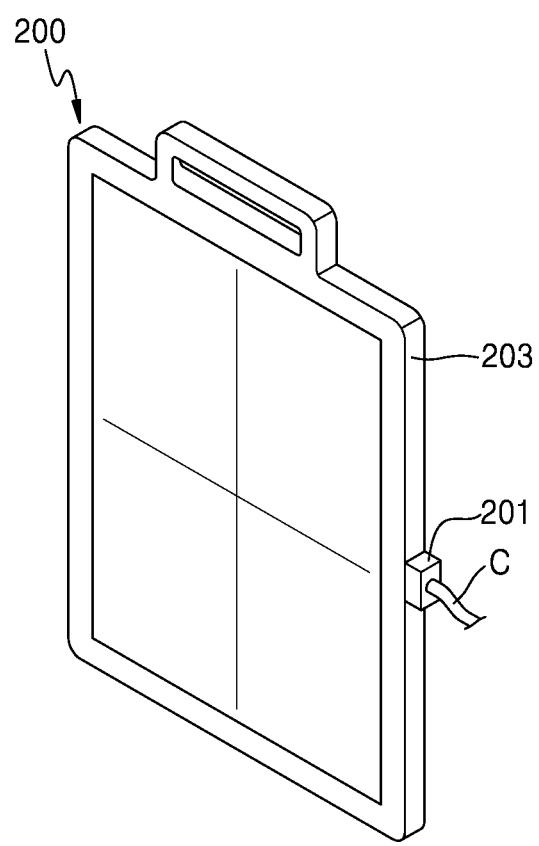
FIG. 2 is a perspective view of a mobile X-ray detector according to an embodiment.

FIG. 2 is a perspective view of the X-ray detector 200 according to an embodiment of the disclosure.

As described above, the X-ray detector 200 used in the X-ray imaging apparatus 100 may be implemented as a portable X-ray detector. The X-ray detector 200 may be equipped with a battery for supplying power to operate wirelessly, or as shown in FIG. 2, may operate by connecting a charging port 201 to a separate power supply via a cable C.

A case 203 may maintain an external appearance of the X-ray detector 200 and may have therein a plurality of detecting elements for detecting X-rays and converting the X-rays into image data, a memory for temporarily or permanently storing the image data, a communication module for receiving a control signal from the X-ray imaging apparatus 100 or transmitting the image data to the X-ray imaging apparatus 100, and a battery. Further, image correction information and intrinsic identification (ID) information of the X-ray detector 200 may be stored in the memory, and the stored ID information may be transmitted together with the image data during communication with the X-ray imaging apparatus 100.

Examples of mobile X-ray detectors will be described in detail with reference to FIGS. 4A, 4B, and 5, according to embodiments.

Figure 3:
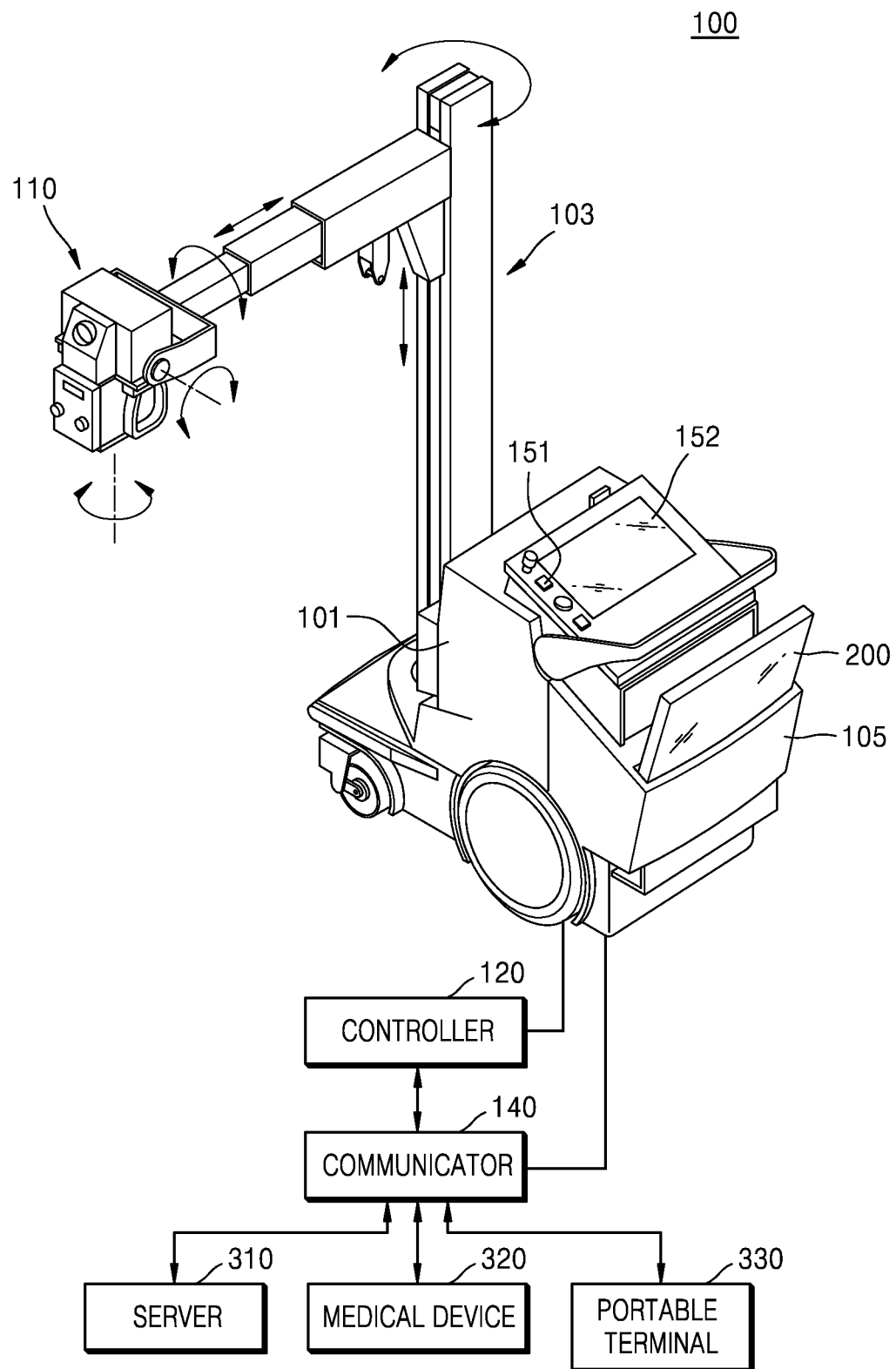
FIG. 3 is an exterior view of a mobile X-ray apparatus according to an embodiment of the disclosure.

FIG. 3 is an exterior view of a mobile X-ray apparatus that is an X ray imaging apparatus according to an embodiment of the disclosure.

The same reference numerals as those in FIG. 1 denote the same elements, and thus a repeated explanation of the reference numerals will be omitted.

An X-ray imaging apparatus may be implemented not only as the ceiling type as described above, but also as a mobile type. When the X-ray imaging apparatus 100 is implemented as a mobile X-ray apparatus, a main body 101 to which the X-ray emitter 110 is connected may freely move and an arm 103 that connects the X-ray emitter 110 and the main body 101 may also be rotated and linearly move, and thus the X-ray emitter 110 may freely move in a three-dimensional (3D) space.

A holder 105 may be formed on the main body 101 to accommodate the X-ray detector 200. A charging terminal may be located in the holder 105 to charge the X-ray detector 200. Thus, the holder 105 may be used to accommodate and charge the X-ray detector 200.

An input device 151, a display 152, the controller 120, and the communicator 140 may be provided on the main body 101. Image data acquired by the X-ray detector 200 may be transmitted to the main body 101 for image processing, and then a resulting image may be displayed on the display 152 or transmitted to an external device via the communicator 140.

The controller 120 and the communicator 140 may be separate from the main body 101, or only some components of the controller 120 and the communicator 140 may be provided on the main body 101.

Figure 4A:
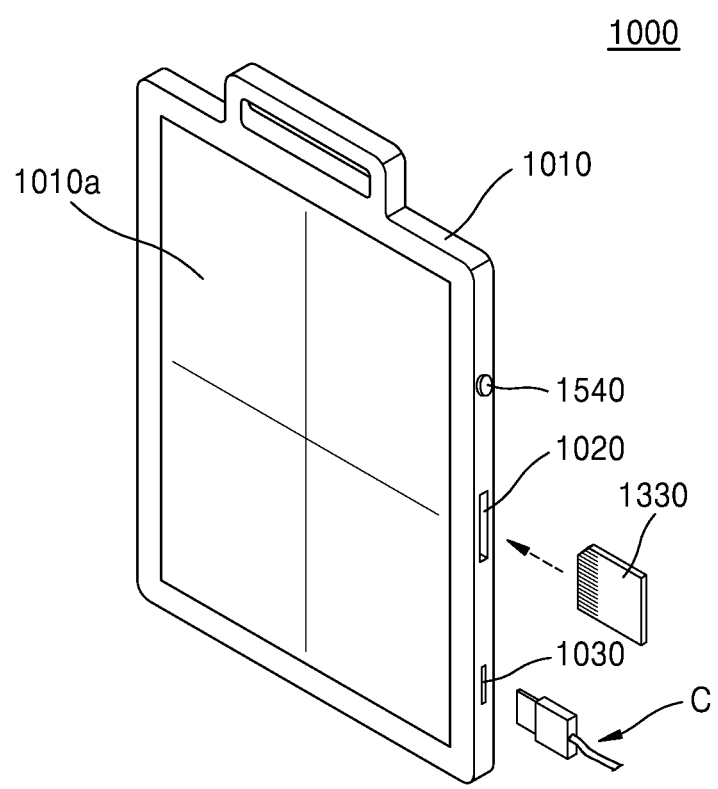
FIG. 4A is a perspective view illustrating a front surface of a mobile X-ray detector according to an embodiment.

FIG. 4A is a perspective view illustrating a front surface of a mobile X-ray detector 1000 according to an embodiment of the disclosure.

Referring to FIG. 4A, the mobile X-ray detector 1000 may include a housing 1010 that surrounds elements, an external memory socket 1020, a charging port 1030, and a power button 1540.

Although the housing 1010 has a rectangular parallelepiped shape in FIG. 4A, the disclosure is not limited thereto.

Figure 4B:
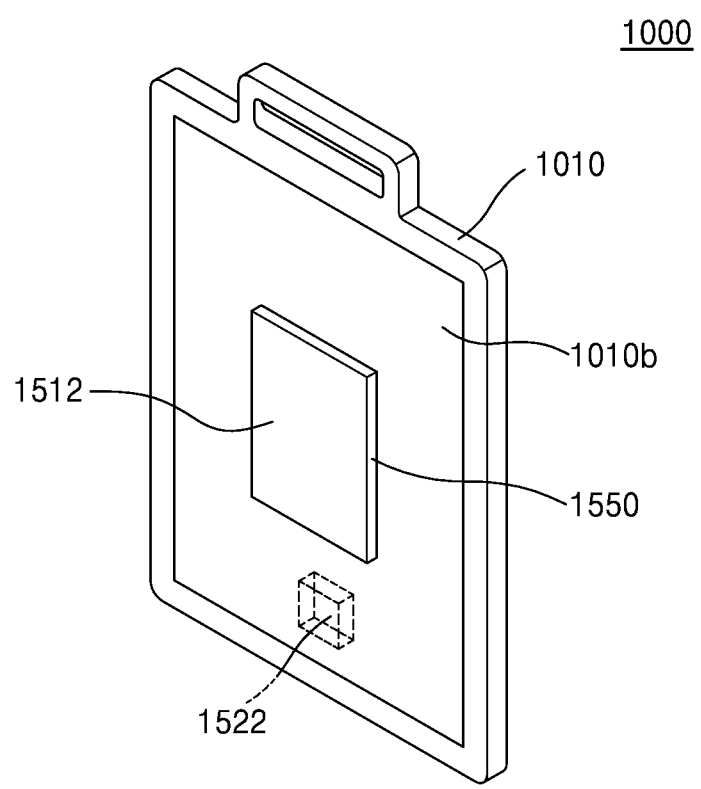
FIG. 4B is a perspective view illustrating a rear surface of a mobile X-ray detector according to an embodiment.

In an embodiment of the disclosure, the housing 1010 may have a rectangular parallelepiped shape having a front surface 1010a on which an X-ray may be incident, a rear surface 1010b, as shown for example in FIG. 4B, facing the front surface 1010a, and four side portions. The housing 1010 may be formed of, for example, a conductive resin. In an embodiment of the disclosure, the housing 1010 may perform an electromagnetic wave shielding function of preventing penetration of electromagnetic waves into the mobile X-ray detector 1000 and radiation of electromagnetic waves from the mobile X-ray detector 1000 to the outside.

A transmission plate may be formed on the front surface 1010a of the housing 1010. The transmission plate may be formed of a carbon material having a light weight, a high stiffness, and a high X-ray transmittance.

The external memory socket 1020 into which an external memory card 1330 is inserted may be formed in a side portion of the housing 1010. The external memory socket 1020 may be formed as an opening in one of the four side portions of the housing 1010.

The charging port 1030 into which a cable C is inserted may be formed in a side portion of the housing 1010. The charging port 1030 may be connected to the cable C, and may receive power from an external power supply through the cable C.

In an embodiment of the disclosure, the charging port 1030 may operate as a connector for transmitting/receiving data by wire to/from a workstation as well as supplying power. In an embodiment of the disclosure, the mobile X-ray detector 1000 may be connected to the workstation through the cable C connected to the charging port 1030, and may transmit/receive imaging information or X-ray image data.

The power button 1540 may be formed on a side portion of the housing 1010 to protrude outward. The power button 1540 may be a button for controlling power on/off of the mobile X-ray detector 1000. In an embodiment of the disclosure, when the mobile X-ray detector 1000 is in an on state and a user presses the power button 1540, a power-off signal for instructing to turn off power of the mobile X-ray detector 1000 may be input to a processor 1200, as shown for example in FIG. 5, and the processor 1200 may identify a time when an input is received at the power button 1540 based on a time when the power-off signal is received. The processor 1200 may determine to turn off power of the mobile X-ray detector 1000 within a predetermined time from the time when the power-off signal is received.

Although not shown in FIG. 4A, an indicator indicating information about an operation state of the mobile X-ray detector 1000 such as an on/off state of a main battery, a capacity of the main battery, or an imaging preparation state may be formed on a side portion of the housing 1010. In an embodiment of the disclosure, the indicator may include a light-emitting diode (LED).

FIG. 4B is a perspective view illustrating a rear surface of the mobile X-ray detector 1000 according to an embodiment of the disclosure.

Referring to FIG. 4B, a main battery 1512 and a battery mount portion 1550 on which the main battery 1512 is mounted may be formed on the rear surface 1010b of the housing 1010. An auxiliary battery 1522 that is not exposed to the outside may be located inside the housing 1010.

The main battery 1512 may supply power to each element of the mobile X-ray detector 1000. The main battery 1512 may include a rechargeable secondary battery. The main battery 1512 may include at least one of, for example, a nickel battery, a lithium-ion battery, a polymer battery, a lithium polymer battery, or a lithium sulfide battery.

The battery mount portion 1550 may be formed on a central portion of the rear surface 1010*b* of the housing 1010. The main battery 1512 may be mounted on the battery mount portion 1550. The main battery 1512 may be detachably mounted on the battery mount portion 1550. Although not shown in FIG. 4B, a locking device for preventing detachment of the main battery 1512 by fixing the main battery 1512 to the battery mount portion 1550 may be formed on the battery mount portion 1550. The locking device may be released by the user's manipulation.

The battery mount portion 1550 may include a sensor for detecting separation or removal of the main battery 1512, for example due to a user's manipulation or due to accidental or unintentional separation. The sensor may include, for example, a photosensitive sensor or a micro switch. The sensor may detect detachment such as separation or removal of the main battery 1512 from the battery mount portion 1550, and may provide to the processor 1200 information about whether and when the main battery 1512 is detached.

The auxiliary battery 1522 may be located in the housing 1010. When the main battery 1512 is separated or removed from the battery mount portion 1550 or a remaining amount of charge of the main battery 1512 is not enough to operate the mobile X-ray detector 1000, the auxiliary battery 1522, instead of the main battery 1512, may supply power to some or all of the elements of the mobile X-ray detector 1000.

Although the auxiliary battery 1522 includes a rechargeable secondary battery, the disclosure is not limited thereto. In an embodiment of the disclosure, the auxiliary battery 1522 may include a rechargeable power storage element such as an electric double-layer condenser, a lithium-ion capacitor, or a super-capacitor.

A power on/off state of the mobile X-ray detector 1000 may be linked to detachment of the main battery 1512 from the battery mount portion 1550. For example, when the main battery 1512 is separated or removed from the battery mount portion 1550, power of the mobile X-ray detector 1000 may be turned off, and when the main battery 1512 is mounted on the battery mount portion 1550 again, power of the mobile X-ray detector 1000 may be turned on. However, the disclosure is not limited thereto, and when the main battery 1512 is separated from the battery mount portion 1550, power may be supplied by the auxiliary battery 1522 or the charging port 1030 to the mobile X-ray detector 1000. When power is supplied by the auxiliary battery 1522, the mobile X-ray detector 1000 may be kept in an on state only for a period of time from when power is supplied by the auxiliary battery 1522 to when power pre-stored in the auxiliary battery 1522 is exhausted. A specific example where power is supplied by the auxiliary battery 1522 according to separation or removal of the main battery 1512 from the battery mount portion 1550 will be described in detail with reference to FIGS. 9A, 9B, and 10.

In FIGS. 4A and 4B, only elements exposed to the outside of the housing 1010 of the mobile X-ray detector 1000 have been described. Examples of elements included in the mobile X-ray detector 1000 but not exposed to the outside will be described in detail with reference to FIG. 5.

Figure 5:
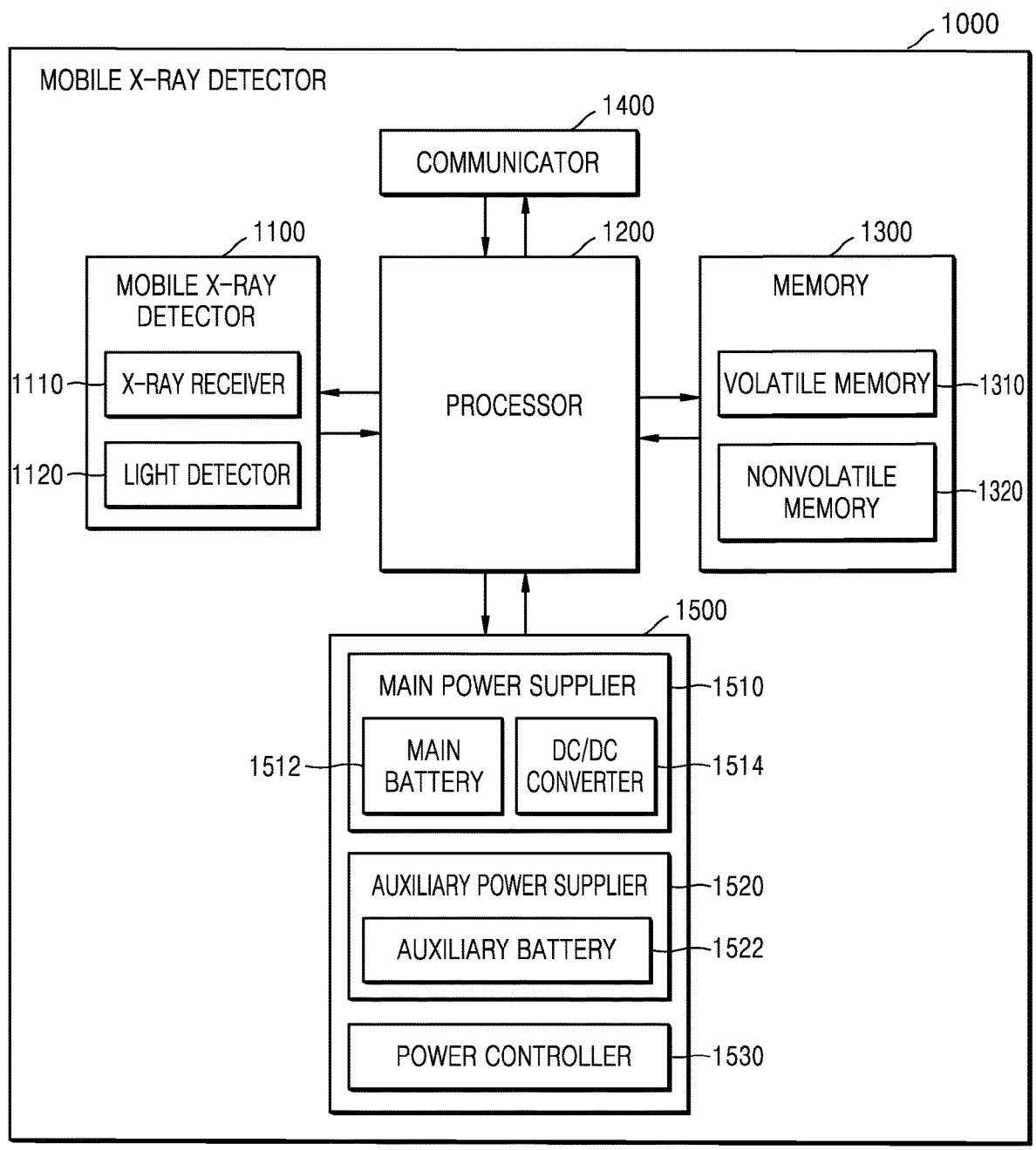
FIG. 5 is a block diagram illustrating examples of elements of a mobile X-ray detector according to an embodiment.

FIG. 5 is a block diagram illustrating elements of the mobile X-ray detector 1000 according to an embodiment of the disclosure.

Referring to FIG. 5, the mobile X-ray detector 1000 may include an X-ray receiver 1100, the processor 1200, a memory 1300, a communicator 1400, and a power supplier 1500. In embodiments, power supplier may refer to a power supply.

The X-ray receiver 1100 may detect an X-ray emitted to an object by an X-ray emitter, for example an X-ray tube, and transmitted through the object, and may generate an electrical signal corresponding to an intensity of the detected X-ray. The X-ray receiver 1100 may include a scintillator 1110 and a light detector 1120.

The scintillator 1110 may convert the X-ray transmitted through the object into visible light and may detect the visible light. The scintillator 1110 may emit photons in a visible wavelength range through reaction with the X-ray incident on the mobile X-ray detector 1000. In an embodiment of the disclosure, when the X-ray receiver 1100 directly converts the X-ray into charges and directly detects the charges, the scintillator 1110 may replace a photon-counting detector.

The light detector 1120 may receive the photons emitted by the scintillator 1110, and may convert the photons into an electrical signal. The light detector 1120 may provide the electrical signal to the processor 1200. The light detector 1120 may include a substrate in which a plurality of pixels are arranged, for example, in a two-dimensional N×M array. The plurality of pixels formed in the substrate of the light detector 1120 may include a photoelectric converter that generates charges according to visible light and accumulates the generated charges and a switching element that is connected to the photoelectric converter and detects the charges accumulated in the photoelectric converter. In an embodiment of the disclosure, the switching element may include, but is not limited to, a thin-film transistor (TFT).

The processor 1200 may generate an X-ray image of the object by using the electrical signal obtained from the X-ray receiver 1100. In an embodiment of the disclosure, the processor 1200 may include an amplifier circuit that amplifies an analog signal obtained from the light detector 1120 and an analog-to-digital converter (ADC) chip that converts the amplified analog signal into a digital signal.

In an embodiment of the disclosure, the processor 1200 may perform a function or an operation by executing program code or instructions stored in the memory 1300. Program code, instructions, or data for performing functions or operations of processing the generated X-ray image may be stored in the memory 1300.

The processor 1200 may include at least one of, but not limited to, a central processing unit, a microprocessor, a graphics processing unit, an application-specific integrated circuit (ASIC), a digital signal processor (DSP), a digital signal processing device (DSPD), a programmable logic device (PLD), or a field programmable gate array (FPGA). In an embodiment of the disclosure, the processor 1200 may include an application processor (AP).

The memory 1300 may include a hardware device that stores program code including data and instructions for performing functions or operations of processing the X-ray image. The memory 1300 may include a volatile memory 1310 and a nonvolatile memory 1320. The volatile memory 1310 may include, for example, a random-access memory (RAM) or a static random-access memory (SRAM). The nonvolatile memory 1320 may include at least one type of storage medium from among, for example, a flash memory, an embedded multimedia card (eMMC), a hard disk, a read-only memory (ROM), an electrically erasable programmable read-only memory (EEPROM), a programmable read-only memory (PROM), a magnetic memory, a magnetic disk, or an optical disk.

Although not shown in FIG. 5, the memory 1300 may further include the external memory card 1330, as shown for example in FIG. 4A. The external memory card 1330 may include a multimedia card micro type or card type memory, for example an SD memory or an XD memory.

Although the processor 1200 and the memory 1300 are separate elements in FIG. 5, the disclosure is not limited thereto. In an embodiment of the disclosure, the processor 1200 and the memory 1300 may be implemented as a single chip.

The processor 1200 may store the generated X-ray image in the volatile memory 1310. After the processor 1200 stores the X-ray image in the volatile memory 1310, the processor 1200 may transmit the X-ray image stored in the volatile memory 1310 to a workstation through the communicator 1400. The X-ray image may be stored in the volatile memory 1310 because an operation speed of the volatile memory 1310 is higher than that of the nonvolatile memory 1320 and thus a storage speed of the X-ray image may be high. However, the X-ray image may be stored in the volatile memory 1310 only once for a certain time, and after the X-ray image is transmitted to the workstation, the X-ray image may be automatically deleted. When there occurs an exceptional situation where power supply from the power supplier 1500 is stopped or cut off and thus the X-ray image stored in the volatile memory 1310 is unable to be transmitted to the workstation, the X-ray image stored in the volatile memory 1310 may be deleted.

In an embodiment of the disclosure, the processor 1200 may receive a signal indicating that power supply by the power supplier 1500 is stopped or cut off from a power controller 1530, and may detect the occurrence of the exceptional situation where the X-ray image is unable to be transmitted to the workstation based on the received signal. When the processor 1200 detects the occurrence of the exceptional situation, the processor 1200 may store the X-ray image in the nonvolatile memory 1320.

In an embodiment of the disclosure, the processor 1200 may determine that the storing of the X-ray image in the nonvolatile memory 1320 is completed, and then may control the power controller 1530 to turn off power of the mobile X-ray detector 1000.

In an embodiment of the disclosure, the processor 1200 may detect a user's input of pressing the power button 1540, as shown for example in FIG. 4A. The processor 1200 may count a time for which the input pressing the power button 1540 lasts, may compare the counted time with a predetermined threshold time, and when the counted time is greater than the threshold time, may control the power controller 1530 to turn off power of the mobile X-ray detector 1000.

In an embodiment of the disclosure, even when the power button 1540 is pressed, until the storing of the X-ray image in the nonvolatile memory 1320 is completed, the processor 1200 may control the power controller 1530 not to transmit a cut-off signal so that it is impossible to turn off power.

In an embodiment of the disclosure, the processor 1200 may recognize a state where the main battery 1512 is removed from the battery mount portion 1550, as shown for example in FIG. 4B, and may control the power controller 1530 to supply power to the X-ray receiver 1100, the processor 1200, the memory 1300, and the communicator 1400 by using the auxiliary power supplier 1520 for a predetermined time from when the removal of the main battery 1512 is detected. The processor 1200 may store the X-ray image in the nonvolatile memory 1320 for the predetermined time.

In an embodiment of the disclosure, the processor 1200 may detect whether the external memory card 1330, as shown for example in FIG. 4A, is inserted into the external memory socket 1020, as shown for example in FIG. 4A. The processor 1200 may identify state information including at least one of a card type of the external memory card 1330, compatibility information with the mobile X-ray detector 1000, capacity information, or information about whether a write operation is possible, and may store the X-ray image in the external memory card 1330 based on the identified state information.

In an embodiment of the disclosure, the processor 1200 may detect that power supply is resumed after the power of the mobile X-ray detector 1000 is turned off, and then may control the communicator 1400 to transmit the X-ray image stored in the nonvolatile memory 1320 to the workstation.

In an embodiment of the disclosure, the processor 1200 may receive imaging information of the X-ray image selected by the user and a request signal for requesting to transmit the X-ray image, from the work station from the workstation through the communicator 1400. The processor 1200 may identify the X-ray image corresponding to the received imaging information from among at least one non-transmitted X-ray image stored in the nonvolatile memory 1320 in response to the received request signal, and may control the communicator 1400 to transmit the identified X-ray image to the workstation.

In an embodiment of the disclosure, the processor 1200 may receive a request signal for requesting to transmit a plurality of thumbnail images of a plurality of X-ray images stored in the nonvolatile memory 1320, from the workstation through the communicator 1400. The processor 1200 may generate a plurality of thumbnail images by performing image conversion on the plurality of images stored in the nonvolatile memory 1320 in response to the received request signal. The processor 1200 may control the communicator 1400 top transmit the generated plurality of thumbnail images to the workstation.

The communicator 1400 may perform data communication by using a wired or wireless communication method with the workstation. The communicator 1400 may perform data communication with the workstation by using at least one of data communication methods including wired local area network (LAN), wireless LAN, Wi-Fi, Bluetooth, Zigbee, Wi-Fi direct (WFD), infrared data association (IrDA), Bluetooth low energy (BLE), near field communication (NFC), wireless broadband Internet (Wibro), world interoperability for microwave access (WiMAX), shared wireless access protocol (SWAP), wireless gigabit alliance (WiGig), and radio frequency (RF) communication.

In an embodiment of the disclosure, the communicator 1400 may receive imaging information about X-ray imaging from the workstation, and may transmit an imaging preparation signal and the currently obtained imaging information. In an embodiment of the disclosure, the communicator 1400 may receive an X-ray imaging instruction signal from the workstation, and may provide the received X-ray imaging instruction signal to the processor 1200.

In an embodiment of the disclosure, the communicator 1400 may transmit the X-ray image to the workstation under the control of the processor 1200.

In an embodiment of the disclosure, the communicator 1400 may transmit imaging information of each of a plurality of X-ray images generated by the processor 1200 and information about transmission to the workstation, under the control of the processor 1200.

The power supplier 1500 may supply power to the X-ray receiver 1100, the processor 1200, the memory 1300, and the communicator 1400. The power supplier 1500 may include a main power supplier 1510, an auxiliary power supplier 1520, and the power controller 1530.

The main power supplier 1510 may include a main battery 1512 and a direct current to direct current (DC/DC) converter 1514. When there does not occur an exceptional situation where, for example, the main battery 1512 is separated or removed from the battery mount portion 1550, as shown for example in FIG. 4B, a remaining amount of charge of the main battery 1512 is not enough to operate the mobile X-ray detector 1000, or the power button 1540, as shown for example in FIG. 4A, is pressed by the user's manipulation, the main battery 1512 may supply driving power to each element of the mobile X-ray detector 1000. The main battery 1512 may include a rechargeable secondary battery. The main battery 1512 may include at least one of, for example, a nickel battery, a lithium-ion battery, a polymer battery, a lithium polymer battery, or a lithium sulfide battery.

The main battery 1512 may supply driving power to the X-ray receiver 1100, the processor 1200, the memory 1300, and the communicator 1400 at a rated voltage of, for example, 12 V.

The DC/DC converter 1514 may convert a voltage of the main battery 1512. The DC/DC converter 1514 may convert a DC voltage applied from the main battery 1512 into a specific driving voltage value according to each element. In an embodiment of the disclosure, the DC/DC converter 1514 may include a plurality of DC/DC converters. In an embodiment of the disclosure, the DC/DC converter 1514 may include a first DC/DC converter that converts 12 V that is the rated voltage of the main battery 1512 into 5 V, a second DC/DC converter that converts the voltage of 5 V into 3.3 V, and a third DC/DC converter that converts the voltage of 5 V into 1.35 V. The voltage of 5V obtained by the first DC/DC converter may be applied to the auxiliary battery 1522. The voltage of 3.3 V obtained by the second DC/DC converter and the voltage of 1.35 V obtained by the third DC/DC converter may be applied to the processor 1200 that may be a low-power CPU and the voltage of 1.35 V may be applied to the memory 1300.

The auxiliary power supplier 1520 may include an auxiliary battery 1522. When an exceptional situation occurs in which the main battery 1512 is separated or removed from the battery mount portion 1550, as shown for example in FIG. 4B, a remaining amount of charge of the main battery 1512 is not enough to operate the mobile X-ray detector 1000, or the power button 1540, as shown for example in FIG. 4A, is pressed by the user, the auxiliary battery 1522, instead of the main battery 1512, may supply driving power to the X-ray receiver 1100, the processor 1200, the memory 1300, and the communicator 1400.

The auxiliary battery 1522 may include a rechargeable secondary battery. For example, the auxiliary battery 1522 may include a lithium (Li)-ion battery. However, the disclosure is not limited thereto, and the auxiliary battery 1522 may include a rechargeable power storage element such as an electric double-layer condenser, a lithium-ion capacitor, or a super-capacitor.

The power controller 1530 may obtain state information of the main power supplier 1510 and the auxiliary power supplier 1520. In an embodiment of the disclosure, the power controller 1530 may recognize a state where the main battery 1512 is removed or separated from the battery mount portion 1550, as shown for example in FIG. 4B. The power controller 1530 may provide information about the state where the main battery 1512 is removed or separated to the processor 1200.

In an embodiment of the disclosure, when the main battery 1512 is removed or separated, the power controller 1530 may switch a power supply source so that a driving voltage is applied by the auxiliary battery 1522 to each element of the mobile X-ray detector 1000 under the control of the processor 1200.

Although not shown in FIG. 5, the power supplier 1500 may receive power from an external power supplier connected through the charging port 1030, as shown for example in FIG. 4A. The power supplier 1500 may charge the main battery 1512 with the power received from the external power supplier or may supply driving power to the X-ray receiver 1100, the processor 1200, the memory 1300, and the communicator 1400.

A conventional mobile X-ray detector generates an X-ray image of an object, stores the generated X-ray image in the volatile memory 1310 by writing the generated X-ray image, and transmits the stored X-ray image to a workstation. However, because the volatile memory 1310 has no limit on the number of updates and is unable to permanently store the X-ray image, when transmission of the X-ray image to the workstation is completed or a new X-ray image is stored, the pre-stored X-ray image is deleted. In particular, when a battery of the conventional mobile X-ray detector has no remaining amount of charge or insufficient amount of charge, the battery is separated, or power is forcibly turned off due to an external input, power supply to the volatile memory 1310 may be cut off and the X-ray image may be lost. When X-ray image data generated by the conventional mobile X-ray detector is lost, re-imaging has to be performed and an X-ray image has to be re-emitted unnecessarily to a patient's body, thereby leading to excessive X-ray emission.

When there occurs an exceptional situation in which the main battery 1512 is separated or removed from the battery mount portion 1550, as shown for example in FIG. 4B, a remaining amount of charge of the main battery 1512 is not enough to operate the mobile X-ray detector 1000, or the power button 1540, as shown for example in FIG. 4A, is pressed by the user and thus the X-ray image is unable to be transmitted to the workstation, the mobile X-ray detector 1000 according to an embodiment of the disclosure may store the X-ray image in the nonvolatile memory 1320, thereby preventing loss of the X-ray image. Because the mobile X-ray detector 1000 may store the X-ray image in the nonvolatile memory 1320, and then when power is re-supplied, the mobile X-ray detector 1000 transmits the X-ray image pre-stored in the nonvolatile memory 1320 to the workstation, excessive X-ray emission due to re-imaging may be prevented. Also, because the mobile X-ray detector 1000 of the disclosure may include the auxiliary battery 1522, the mobile X-ray detector 1000 may maintain power for a certain time even in an unexpected situation in which power of the main battery 1512 is cut off and may store the X-ray image in the nonvolatile memory 1320 for a certain time.

Figure 6:
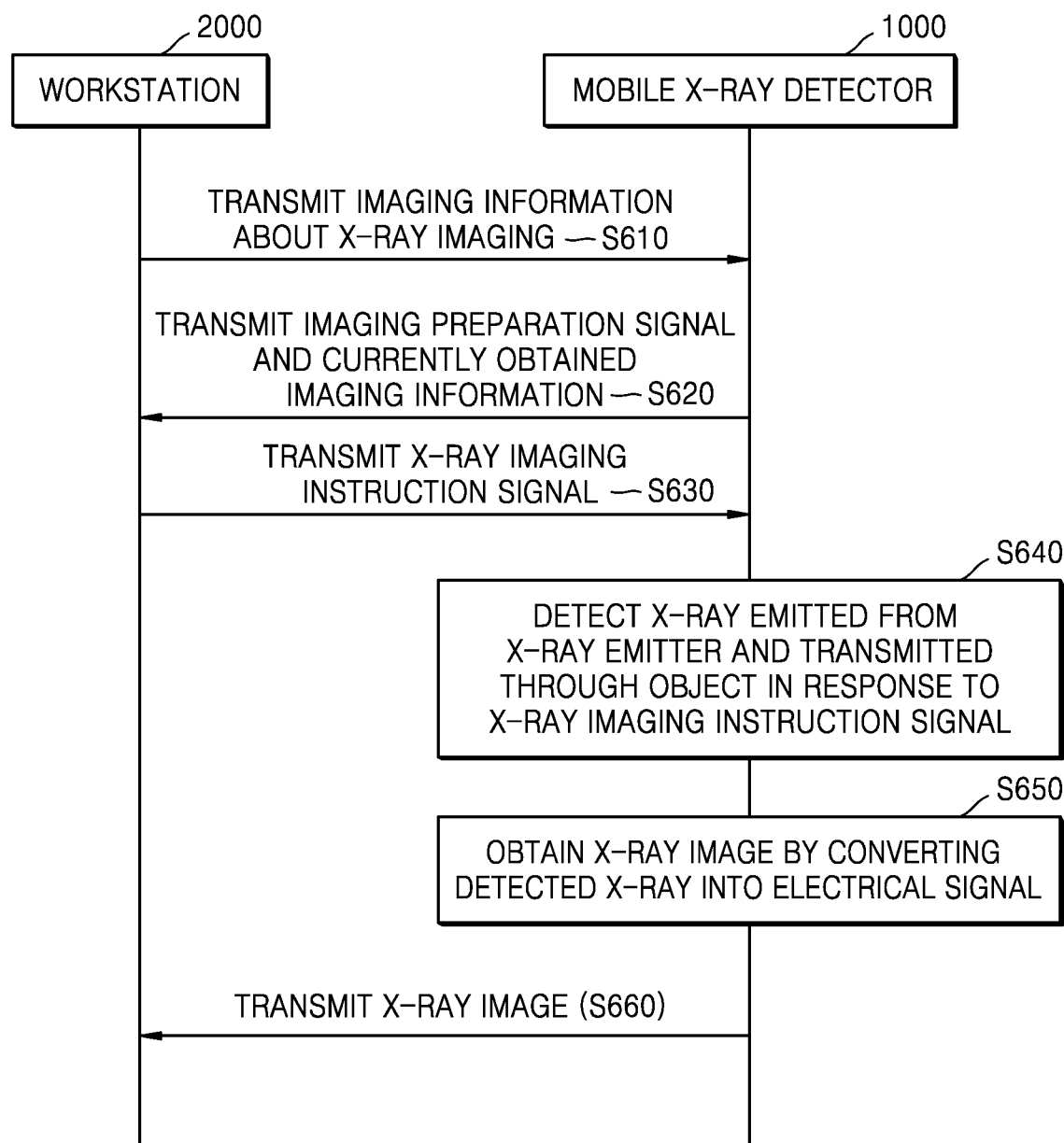
FIG. 6 is a flowchart of a method by which an X-ray imaging apparatus obtains an X-ray image of an object, according to an embodiment.

FIG. 6 is a flowchart of a method by which an X-ray imaging apparatus obtains an X-ray image of an object according to an embodiment of the disclosure.

Referring to FIG. 6, an X-ray imaging apparatus may include the mobile X-ray detector 1000 and the workstation 2000. Although not shown in FIG. 6, the X-ray imaging apparatus may further include an X-ray emitter, for example an X-ray tube, that generates an X-ray and emits the generated X-ray.

The workstation 2000 may receive a command or the like from a user and may transmit a control signal for controlling the X-ray emitter and the mobile X-ray detector 1000 to the X-ray emitter and the mobile X-ray detector 1000 based on the received command of the user. The workstation 2000 may include a controller 2200, as shown for example in FIG. 14, that controls the X-ray imaging apparatus according to the command and a communicator 2400, as shown for example in FIG. 14, that communicates with an external device. The workstation 2000 may further include a user input interface 2100, as shown for example in FIG. 14, that receives the user's command and a display 2300, as shown for example in FIG. 14, that displays a user interface (UI) for obtaining an X-ray image and manipulating the X-ray image, in addition to the controller 2200 and the communicator 2400. An example of a workstation 2000 will be described in detail with reference to FIG. 14.

In operation S610 of FIG. 6, the workstation 2000 transmits imaging information about X-ray imaging to the mobile X-ray detector 1000. In an embodiment of the disclosure, the workstation 2000 may receive user input includes an input of imaging information required for X-ray imaging through the user input interface 2100, as shown for example in FIG. 14, and the controller 2200, as shown for example in FIG. 14, may receive the imaging information from the user input interface 2100. The imaging information may include information about at least one of, for example, patient identification information (patient ID), an imaging protocol, imaging conditions, or an imaging timing. The communicator 2400, as shown for example in FIG. 14, of the workstation 2000 may transmit the imaging information to the mobile X-ray detector 1000.

In operation S620, the mobile X-ray detector 1000 transmits an imaging preparation signal and the currently obtained imaging information. In an embodiment of the disclosure, the mobile X-ray detector 1000 may detect an X-ray, may identify a state where an X-ray image of an object may be generated, and may transmit information about the identified state to the workstation 2000.

In operation S630, the workstation 2000 transmits an X-ray imaging instruction signal to the mobile X-ray detector 1000. In an embodiment of the disclosure, the workstation 2000 may transmit an imaging instruction signal to the X-ray emitter through the communicator 2400, as shown for example in FIG. 14. The controller 2200, as shown for example in FIG. 14, of the workstation 2000 may control the imaging timing and the imaging conditions of the X-ray emitter, and may control a position or a direction of the X-ray emitter according to a position of an imaging target portion of the patient and the imaging protocol.

In operation S640, the mobile X-ray detector 1000 detects the X-ray emitted from the X-ray emitter and transmitted through the object, in response to the X-ray imaging instruction signal. In an embodiment of the disclosure, the mobile X-ray detector 1000 may detect the X-ray transmitted through the object through the X-ray receiver 1100, as shown for example in FIG. 5, and may generate an electrical signal corresponding to an intensity of the detected X-ray.

In operation S650, the mobile X-ray detector 1000 obtains an X-ray image by converting the detected X-ray into an electrical signal. In an embodiment of the disclosure, the processor 1200, as shown for example in FIG. 5, of the mobile X-ray detector 1000 may generate the X-ray image of the object by amplifying the electrical signal that is an analog signal and converting the amplified electrical signal into a digital signal.

In an embodiment of the disclosure, the mobile X-ray detector 1000 may temporarily store the obtained X-ray image in the volatile memory 1310, as shown for example in FIG. 5.

In operation S660, the mobile X-ray detector 1000 transmits the obtained X-ray image to the workstation 2000.

There may occur an exceptional situation in which the mobile X-ray detector 1000 is unable to transmit the X-ray image to the workstation 2000 in operation S660, an example of which will be described in detail with reference to FIG. 7.

Figure 7:
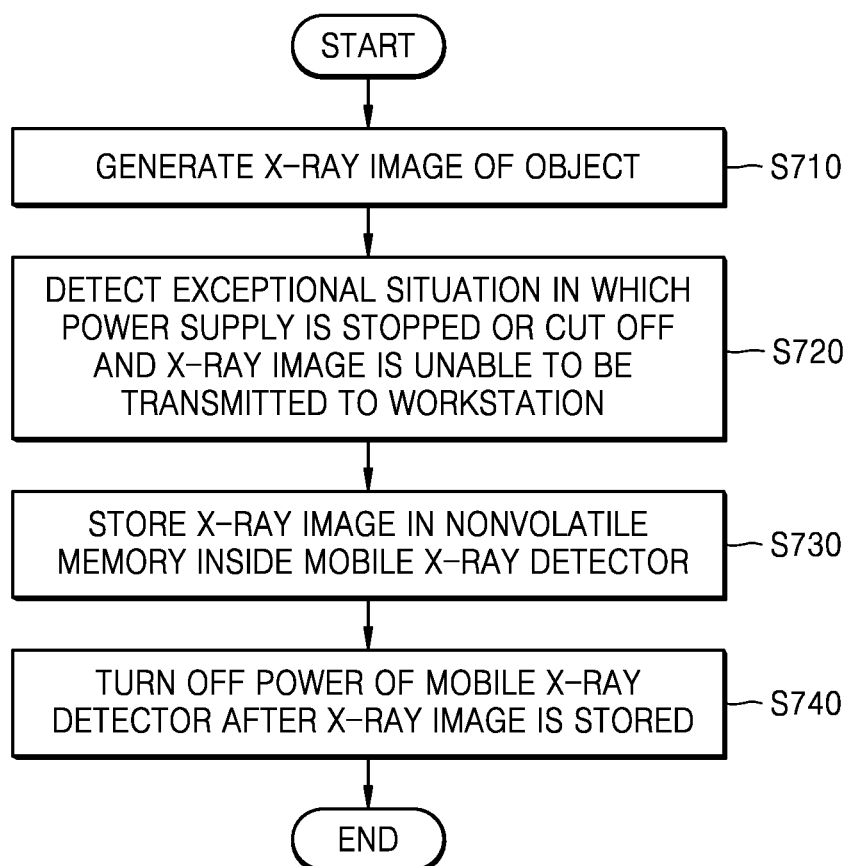
FIG. 7 is a flowchart of an operating method of a mobile X-ray detector, according to an embodiment.

FIG. 7 is a flowchart of an operating method of the mobile X-ray detector 1000 according to an embodiment of the disclosure.

In operation S710, the mobile X-ray detector 1000 generates an X-ray image of an object. In an embodiment of the disclosure, the processor 1200, as shown for example in FIG. 5, of the mobile X-ray detector 1000 may temporarily store the generated X-ray image in the volatile memory 1310, as shown for example in FIG. 5.

In operation S710, the mobile X-ray detector 1000 may transmit the X-ray image stored in the volatile memory 1310 to the workstation 2000, as shown for example in FIG. 6.

In operation S720, the mobile X-ray detector 1000 detects an exceptional situation in which power supply is stopped or cut off and thus the X-ray image is unable to be transmitted to the workstation 2000. In an embodiment of the disclosure, the mobile X-ray detector 1000 may detect an occurrence of an exceptional situation in which the main battery 1512, as shown for example in FIG. 5, is separated or removed from the battery mount portion 1550, as shown for example in FIG. 4B, a remaining amount of charge of the main battery 1512 is not enough to operate each element of the mobile X-ray detector 1000, or the power button 1540, as shown for example in FIG. 4A, is pressed due to a user's manipulation.

In an embodiment of the disclosure, the processor 1200 of the mobile X-ray detector 1000 may receive an input pressing the power button 1540 due to the user's manipulation, and may count a time elapsed from a time when the input pressing the power button 1540 is received. An example of a specific method of processing the X-ray image according to the input pressing the power button 1540 will be described with reference to FIG. 8.

In an embodiment of the disclosure, the processor 1200, as shown for example in FIG. 5, of the mobile X-ray detector 1000 may receive a detection signal indicating that the main battery 1512 is separated or removed from the battery mount portion 1550 from a sensor included in the battery mount portion 1550, and may detect detachment of the main battery 1512 based on the received detection signal. An example of the detection of the detachment of the main battery 1512 and a specific operating method of the mobile X-ray detector 1000 after the detection will be described with reference to FIGS. 9A, 9B, and 10.

In operation S730, the mobile X-ray detector 1000 stores the X-ray image in a nonvolatile memory inside the mobile X-ray detector 1000. The nonvolatile memory may include at least one type of storage medium from among a flash memory, eMMC, a hard disk, a ROM, EEPROM, PROM, a magnetic memory, a magnetic disk, or an optical disk.

In operation S740, the mobile X-ray detector 1000 turns off power of the mobile X-ray detector 1000 after the X-ray image is stored. In an embodiment of the disclosure, the processor 1200, as shown for example in FIG. 5, of the mobile X-ray detector 1000 may determine whether the X-ray image is stored in the nonvolatile memory by scanning the nonvolatile memory. After the processor 1200 determines that the storing of the X-ray image in the nonvolatile memory is completed, the processor 1200 may control the power supplier 1500, as shown for example in FIG. 5, to turn off power of the mobile X-ray detector 1000.

In an embodiment of the disclosure, even when the processor 1200 receives a signal indicating that a user input pressing the power button 1540 is detected, the processor 1200 may determine whether the X-ray image is stored in the nonvolatile memory without immediately turning off power, and after it is determined that the storing of the X-ray image is completed, the processor 1200 may control the power supplier 1500 to turn off power.

Figure 8:
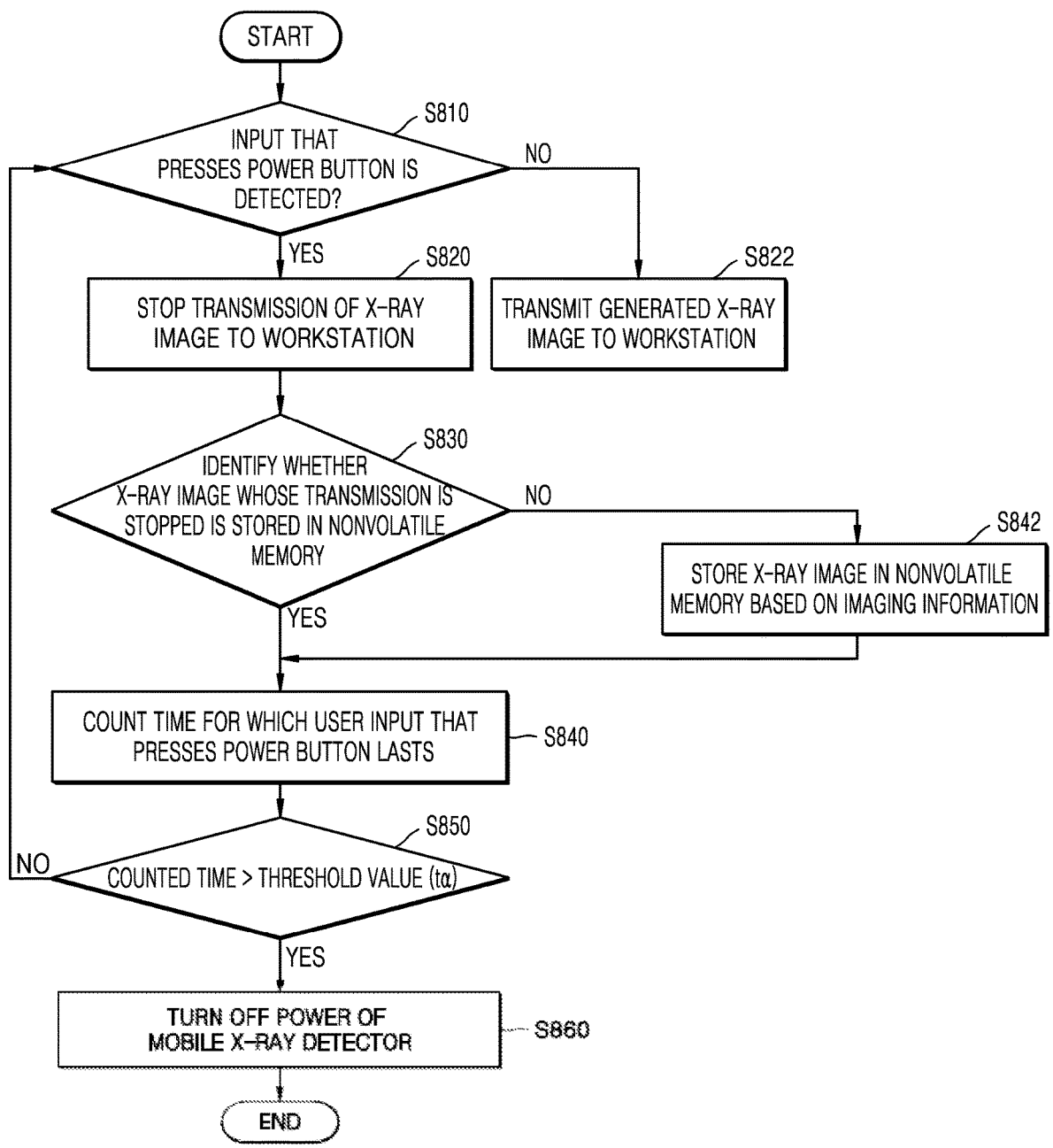
FIG. 8 is a flowchart of a method by which a mobile X-ray detector turns off power according to an input pressing a power button, according to an embodiment.

FIG. 8 is a flowchart of a method by which the mobile X-ray detector 1000 turns off power according to an input pressing the power button 1540, as shown for example in FIG. 4A, according to an embodiment of the disclosure.

In operation S810, the mobile X-ray detector 1000 detects an input of pressing the power button 1540. In an embodiment of the disclosure, when the mobile X-ray detector 1000 is in an on state and the power button 1540 is pressed due to a user's manipulation, the processor 1200, as shown for example in FIG. 5, of the mobile X-ray detector 1000 may obtain a power-off signal for instructing to turn off power from the power button 1540. The processor 1200 may detect the input pressing the power button 1540 based on the obtained power-off signal. In an embodiment of the disclosure, the processor 1200 may obtain information about a time when the power button 1540 is pressed due to the user's manipulation, based on a time when the power-off signal is obtained.

When the input pressing the power button is detected, at operation S820 the mobile X-ray detector 1000 stops transmission of an X-ray image to the workstation 2000. In an embodiment of the disclosure, the mobile X-ray detector 1000 may identify imaging information of the X-ray image for which transmission is stopped. For example, the mobile X-ray detector 1000 may identify at least one information from among patient identification information, an imaging protocol, imaging conditions, or an imaging timing of the X-ray image whose transmission is stopped and that is not normally transmitted to the workstation 2000.

When the input pressing the power button is not detected, at operation S822 the mobile X-ray detector 1000 transmits the generated X-ray image to the workstation 2000.

In operation S830, the mobile X-ray detector 1000 identifies whether the X-ray image whose transmission is stopped is stored in a nonvolatile memory. In an embodiment of the disclosure, the processor 1200 of the mobile X-ray detector 1000 may determine whether the non-transmitted X-ray image whose transmission to the workstation 2000 is stopped is stored in the nonvolatile memory by scanning the nonvolatile memory. In an embodiment of the disclosure, the processor 1200 may scan the nonvolatile memory based on the imaging information of the non-transmitted X-ray image identified in operation S820, and may determine whether the X-ray image corresponding to the imaging information of the non-transmitted X-ray image is stored in the nonvolatile memory.

When the processor 1200 determines that the X-ray image whose transmission is stopped is stored in the nonvolatile memory, at operation S840 the mobile X-ray detector 1000 counts a time for which the user input pressing the power button lasts. In an embodiment of the disclosure, the processor 1200 of the mobile X-ray detector 1000 may determine that the input continuously presses the power button 1540 from a time when the power-off signal is obtained from the power button 1540 is received, and may count a time elapsed while the power button 1540 is pressed.

When it is determined that the X-ray image whose transmission is stopped is not stored in the nonvolatile memory, at operation S842 the mobile X-ray detector 1000 identifies the non-transmitted X-ray image based on the imaging information and stores the non-transmitted X-ray image in the nonvolatile memory.

In operation S850, the mobile X-ray detector 1000 compares the counted time with a predetermined threshold value ($t_\alpha$). The predetermined threshold value ($t_\alpha$) may be a set time value and may be, for example, but is not limited to, 5 seconds.

When the counted time is greater than the predetermined threshold value ($t_\alpha$), at operation S860 power of the mobile X-ray detector 1000 is turned off. In an embodiment of the disclosure, when the counted time is greater than the predetermined threshold value ($t_\alpha$), the processor 1200 of the mobile X-ray detector 1000 may control the power supplier 1500, as shown for example in FIG. 5, to cut off driving power supplied to the processor 1200, the memory 1300, as shown for example in FIG. 5, and the communicator 1400, as shown for example in FIG. 5.

When the counted time is less than the predetermined threshold value ($t_\alpha$), the mobile X-ray detector 1000 returns to operation S810 in which the input pressing the power button 1540 is detected.

Figure 9A:
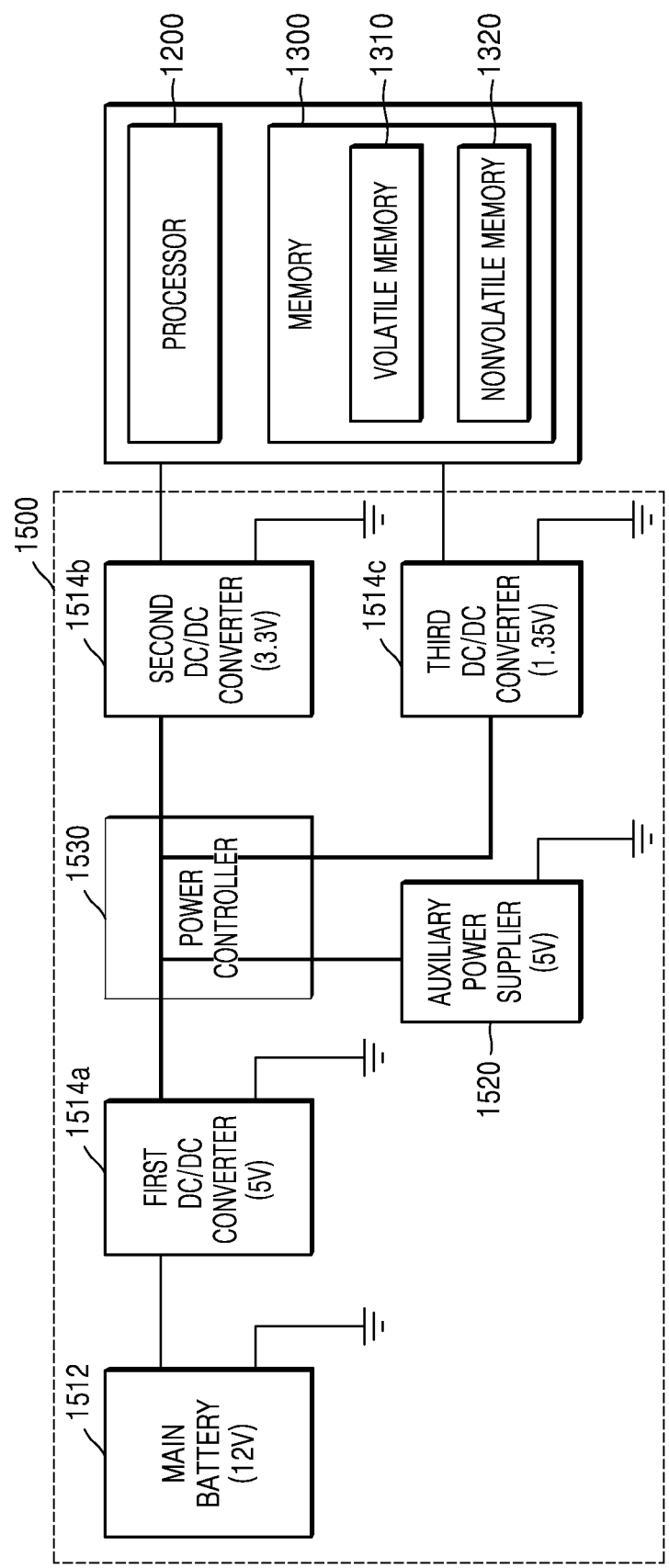
FIG. 9A is a circuit diagram of a power supplier inside a mobile X-ray detector, according to an embodiment.

FIG. 9A is a circuit diagram of the power supplier 1500 inside the mobile X-ray detector 1000 according to an embodiment of the disclosure.

Referring to FIG. 9A, the power supplier 1500 may include the main battery 1512, the auxiliary power supplier 1520, a first DC/DC converter 1514a, a second DC/DC converter 1514b, a third DC/DC converter 1514c, and the power controller 1530.

The main battery 1512 may include a rechargeable secondary battery. In an embodiment of the disclosure, the main battery 1512 may supply driving power to the processor 1200 and the memory 1300 at a rated voltage of 12 V.

The first DC/DC converter 1514a may convert a voltage of the main battery 1512. The first DC/DC converter 1514a may convert a direct current (DC) voltage of 12 V applied from the main battery 1512 into 5 V. In an embodiment of the disclosure, the processor 1200 that is a low-power processor may be designed to receive a driving voltage of 5 V. The first DC/DC converter 1514a may receive the voltage of 12 V output from the main battery 1512 and may down-convert the voltage of 12 V into 5 V.

The power controller 1530 may control supply of the voltage of 5 V output through the first DC/DC converter 1514a. In an embodiment of the disclosure, the power controller 1530 may receive the voltage of 5 V from the first DC/DC converter 1514a, may supply part of the voltage to the auxiliary power supplier 1520, and may supply remaining part of the voltage to the second DC/DC converter 1514b and the third DC/DC converter 1514c.

In an embodiment of the disclosure, the power controller 1530 may obtain state information of the main battery 1512 and the auxiliary power supplier 1520. In an embodiment of the disclosure, the power controller 1530 may recognize a state where the main battery 1512 is removed or separated from the battery mount portion 1550, as shown for example in FIG. 4B, and may provide information about the recognized state to the processor 1200. In an embodiment of the disclosure, the power controller 1530 may switch power to apply a driving voltage to the processor 1200 and the memory 1300 through the auxiliary power supplier 1520, according to a control signal obtained from the processor 1200, which will be described in detail with reference to FIG. 9B.

The second DC/DC converter 1514b may convert the voltage of 5 V received from the first DC/DC converter

1514a into 3.3 V. The second DC/DC converter 1514b may supply the voltage of 3.3 V as a driving voltage for driving the processor 1200.

The third DC/DC converter 1514c may convert the voltage of 5 V received from the first DC/DC converter 1514a into 1.35 V. The third DC/DC converter 1514c may supply the voltage of 1.35 V as a driving voltage for driving the processor 1200 and the memory 1300.

The auxiliary power supplier 1520 may include the auxiliary battery 1522, as shown for example in FIG. 5. In an embodiment of the disclosure, the auxiliary battery 1522 may be a rechargeable secondary battery. For example, the auxiliary battery 1522 may include a Li-ion battery. In another embodiment of the disclosure, the auxiliary power supplier 1520 may include a rechargeable power storage element such as an electric double-layer condenser, a lithium-ion capacitor, or a super-capacitor. The auxiliary power supplier 1520 may perform charging by using the voltage of 5 V received from the first DC/DC converter 1514a.

Figure 9B:
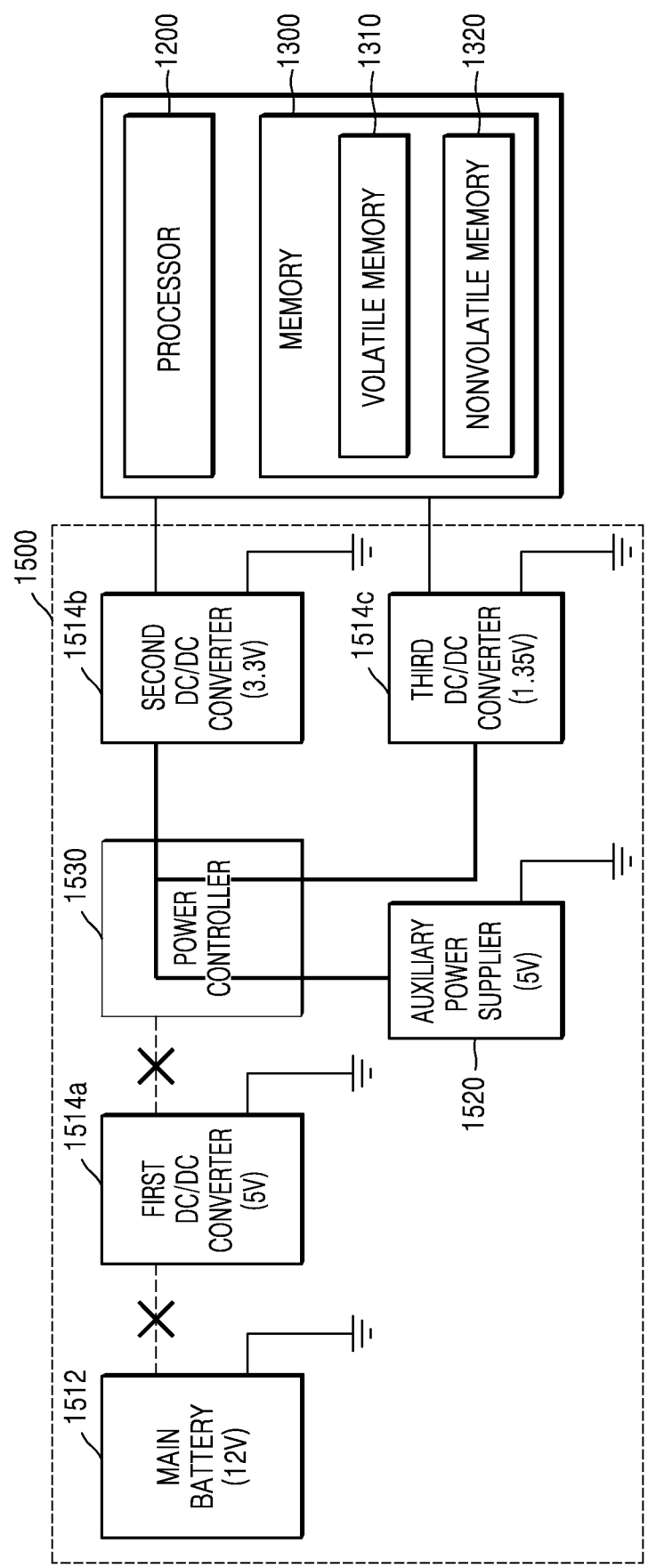
FIG. 9B is a circuit diagram of a power supplier inside a mobile X-ray detector, according to an embodiment.

FIG. 9B is a circuit diagram of the power supplier 1500 inside the mobile X-ray detector 1000 according to an embodiment of the disclosure.

FIG. 9B is a diagram for describing an operating method of the power supplier 1500 when a main battery (12 V) is removed or separated in FIG. 9A. Accordingly, the same elements as those in FIG. 9A will not be repeatedly described.

Referring to FIG. 9B, the main battery 1512 may be removed or separated from the battery mount portion 1550, as shown for example in FIG. 4B. When the main battery 1512 is removed or separated, the processor 1200 may obtain information about detachment of the main battery 1512 from a sensor of the battery mount portion 1550, and may provide the information about the detachment of the main battery 1512 to the power controller 1530. The power controller 1530 may cut off connection with the first DC/DC converter 1514a based on the information obtained from the processor 1200, and may switch power to apply a driving voltage to the processor 1200 and the memory 1300 through the auxiliary power supplier 1520.

The auxiliary power supplier 1520 may supply power pre-stored in the auxiliary battery 1522, as shown for example in FIG. 5, or a super-capacitor to the processor 1200 and the memory 1300. The auxiliary power supplier 1520 may supply a driving voltage to the processor 1200 and the memory 1300 for a predetermined time from when separation or removal of the main battery 1512 is recognized. In an embodiment of the disclosure, the auxiliary power supplier 1520 may supply a driving voltage to the X-ray receiver 1100, as shown for example in FIG. 5, and the communicator 1400, as shown for example in FIG. 5, as well as the processor 1200 and the memory 1300. The predetermined time may be a time from when a driving voltage is supplied to the X-ray receiver 1100, the processor 1200, the memory 1300, and the communicator 1400 by using power pre-stored in the auxiliary power supplier 1520 to when the pre-stored power is exhausted. The predetermined time may be set to vary according to a power storage capacity of the auxiliary power supplier 1520.

The processor 1200 may store an X-ray image in the nonvolatile memory 1320 for the predetermined time, an example of which will be described in detail with reference to FIG. 10.

Figure 10:
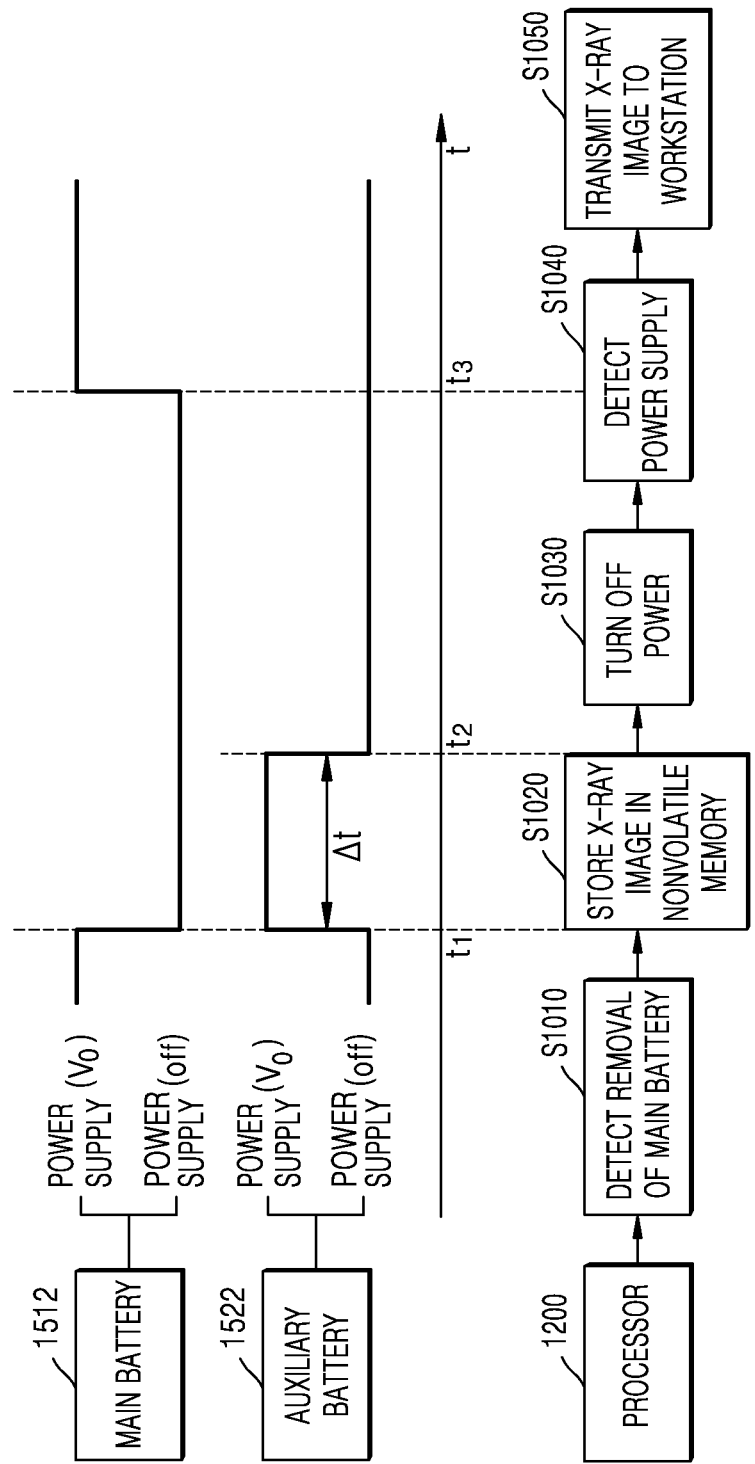
FIG. 10 is a diagram illustrating an operation performed by a mobile X-ray detector based on a power supply state of the power supplier, according to an embodiment.

FIG. 10 is a diagram illustrating an operation performed by the processor 1200 of the mobile X-ray detector 1000 based on a power supply state of the power supplier 1500 over time according to an embodiment of the disclosure.

Referring to FIG. 10, the power supplier 1500 may include the main battery 1512 and the auxiliary battery 1522.

In operation S1010, the processor 1200 detects removal of the main battery 1512 at a time $t_1$. Although the main battery 1512 supplies a driving voltage $V_0$ before the time $t_1$ to each element of the mobile X-ray detector 1000, the main battery 1512 may be removed or separated from the battery mount portion 1550, as shown for example in FIG. 4B, at the time $t_1$. The driving voltage $V_0$ may be a voltage for driving the X-ray receiver 1100, the processor 1200, the memory 1300, and the communicator 1400, as shown for example in FIG. 5. In an embodiment of the disclosure, the driving voltage $V_0$ may be a sum of a voltage of 3.3 V and a voltage of 1.35 V for driving the processor 1200 and the memory 1300, as shown for example in FIGS. 9A and 9B. The processor 1200 may obtain information indicating that the main battery 1512 is removed or separated at the time $t_1$ through a sensor of the battery mount portion 1550.

In the example shown in FIG. 10, the auxiliary battery 1522, instead of the main battery 1512, supplies the driving voltage $V_0$ to the X-ray receiver 1100, the processor 1200, the memory 1300, and the communicator 1400 at the time $t_1$. In an embodiment of the disclosure, the auxiliary battery 1522 may supply the driving voltage $V_0$ to the processor 1200 and the memory 1300 at the time $t_1$ when the removal or separation of the main battery 1512 is detected under the control of the power controller 1530, as shown for example in FIGS. 9A and 9B.

In operation S1020, the processor 1200 stores an X-ray image in the nonvolatile memory 1320, as shown for example in FIGS. 9A and 9B. In an embodiment of the disclosure, the processor 1200 may store the X-ray image in the nonvolatile memory 1320 for a predetermined duration ($\Delta t$) between the time $t_1$ when the removal of the main battery 1512 is detected and a time $t_2$. The predetermined duration ($\Delta t$) may be a duration for which the driving voltage may be supplied to the elements, e.g., the X-ray receiver 1100, the processor 1200, the memory 1300, and the communicator 1400, of the mobile X-ray detector 1000 by using the auxiliary battery 1522. The predetermined duration ($\Delta t$) may be a period of time during which power pre-stored in the auxiliary battery 1522 is exhausted, and may be set to vary according to a power storage capacity of the auxiliary battery 1522.

In operation S1030, the processor 1200 turns off power after the time $t_2$ when the power pre-stored in the auxiliary battery 1522 is completely exhausted. In an embodiment of the disclosure, before the time $t_2$, the processor 1200 may determine whether the storing of the X-ray image in the nonvolatile memory 1320 is completed. After the processor 1200 determines that the storing of the X-ray image is completed, the processor 1200 may control the power controller 1530, as shown for example in FIGS. 9A and 9B, to cut off the driving voltage supplied to the X-ray receiver 1100, the processor 1200, the memory 1300, and the communicator 1400, as shown for example in FIG. 5.

In operation S1040, the processor 1200 detects that power is re-supplied. In an embodiment of the disclosure, when the main battery 1512 is re-mounted or the driving voltage is applied from an external power supplier at a time $t_3$, the processor 1200 may obtain a signal indicating that power supply is resumed from the power controller 1530.

In operation S1050, the processor 1200 transmits the X-ray image to a workstation. In an embodiment of the disclosure, the processor 1200 may control the communicator 1400, as shown for example in FIG. 5, to transmit the X-ray image stored in the nonvolatile memory 1320 to the workstation. In an embodiment of the disclosure, the processor 1200 may control the communicator 1400 to transmit imaging information of each X-ray image stored in the nonvolatile memory 1320 to the workstation.

Figure 11:
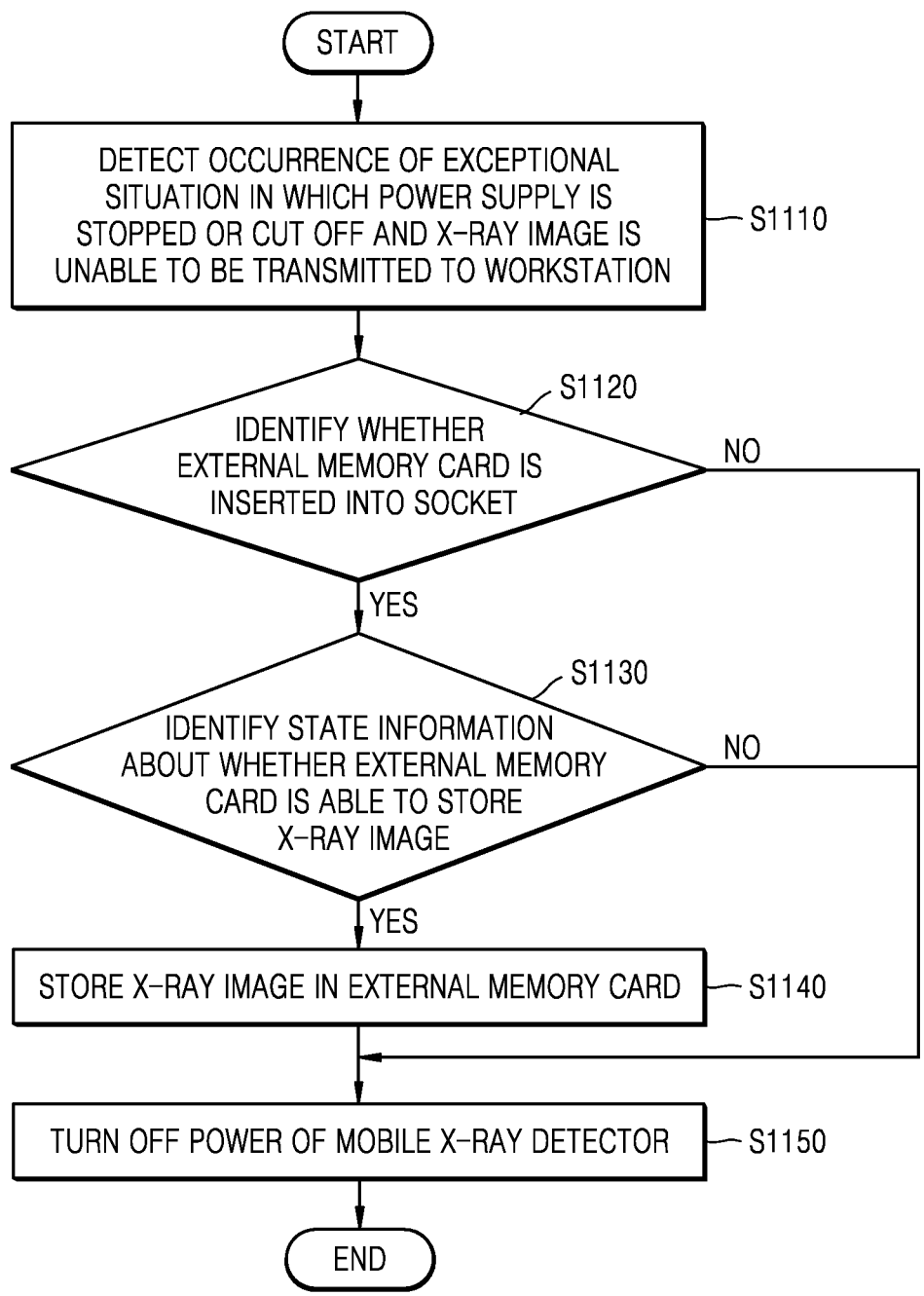
FIG. 11 is a flowchart of a method of turning off power when power supply to a mobile X-ray detector is stopped or cut off, according to an embodiment.

FIG. 11 is a flowchart of a method of turning off power when power supply to the mobile X-ray detector 1000 is stopped or cut off according to an embodiment of the disclosure.

In operation S1110, the mobile X-ray detector 1000 detects an occurrence of an exceptional situation in which power supply is stopped or cut off and thus an X-ray image is unable to be transmitted to a workstation. In an embodiment of the disclosure, the mobile X-ray detector 1000 may detect an occurrence of an exceptional situation in which the main battery 1512, as shown for example in FIG. 5, is separated or removed from the battery mount portion 1550, as shown for example in FIG. 4B, a remaining amount of charge of the main battery 1512 is not enough to operate each element of the mobile X-ray detector 1000, or the power button 1540, as shown for example in FIG. 4A, is pressed due to a user's manipulation. Before operation S1110, the mobile X-ray detector 1000 may generate an X-ray image of an object by detecting an X-ray emitted by an X-ray emitter to the object and transmitted through the object. The mobile X-ray detector 1000 may store the generated X-ray image in a volatile memory.

In operation S1120, the mobile X-ray detector 1000 identifies whether the external memory card 1330, as shown for example in FIG. 4A, is inserted into the external memory socket 1020, as shown for example in FIG. 4A. The external memory card 1330 may include at least one of, for example, a multimedia card micro type or card type memory, for example a secure digital (SD) memory or an extreme digital (XD) memory. The external memory card 1330 may be separated from the external memory socket 1020, when the external memory card 1330 is not normally mounted on the external memory socket 1020 due to its low durability or when the mobile X-ray detector 1000 falls to the floor due to poor manipulation. The processor 1200 may monitor a state of the external memory socket 1020, and may determine whether the external memory card 1330 is appropriately inserted by accessing the external memory card 1330 through the external memory socket 1020.

When the controller 120 determines that the external memory card 1330 is inserted into the external memory socket 1020, at operation S1130 the mobile X-ray detector 1000 identifies state information about whether the external memory card 1330 may store the X-ray image. In an embodiment of the disclosure, the processor 1200, as shown for example in FIG. 5, of the mobile X-ray detector 1000 may identify state information including at least one of a card type of the external memory card 1330 inserted into the external memory socket 1020, compatibility information with the mobile X-ray detector 1000, capacity information, or information about whether a write operation is possible. The processor 1200 may determine whether the external memory card 1330 may store the X-ray image based on the identified state information. For example, the processor 1200 may determine whether the external memory card 1330 may store the X-ray image by identifying residual capacity information of the external memory card 1330 and comparing the residual capacity information with a file size of the X-ray image.

After the state information of the external memory card 1330 is identified, at operation S1140 the mobile X-ray detector 1000 stores the X-ray image in the external memory card 1330. In an embodiment of the disclosure, the processor 1200 may store, in the external memory card 1330, the X-ray image that is temporarily stored in a volatile memory.

In operation S1150, the mobile X-ray detector 1000 turns off power. In an embodiment of the disclosure, the processor 1200 may determine whether the X-ray image is stored in the external memory card 1330 by scanning the external memory card 1330 through the external memory socket 1020. After the processor 1200 determines that the storing of the X-ray image in the external memory card 1330 is completed, the processor 1200 may control the power supplier 1500, as shown for example in FIG. 5, to turn off power of the mobile X-ray detector 1000.

When it is identified in operation S1120 that the external memory card 1330 is not inserted into the external memory socket 1020 or when it is identified in operation S1130 that the external memory card 1330 is unable to store the X-ray image, the processor 1200 may turn off power of the mobile X-ray detector 1000 at operation S1150.

Figure 12:
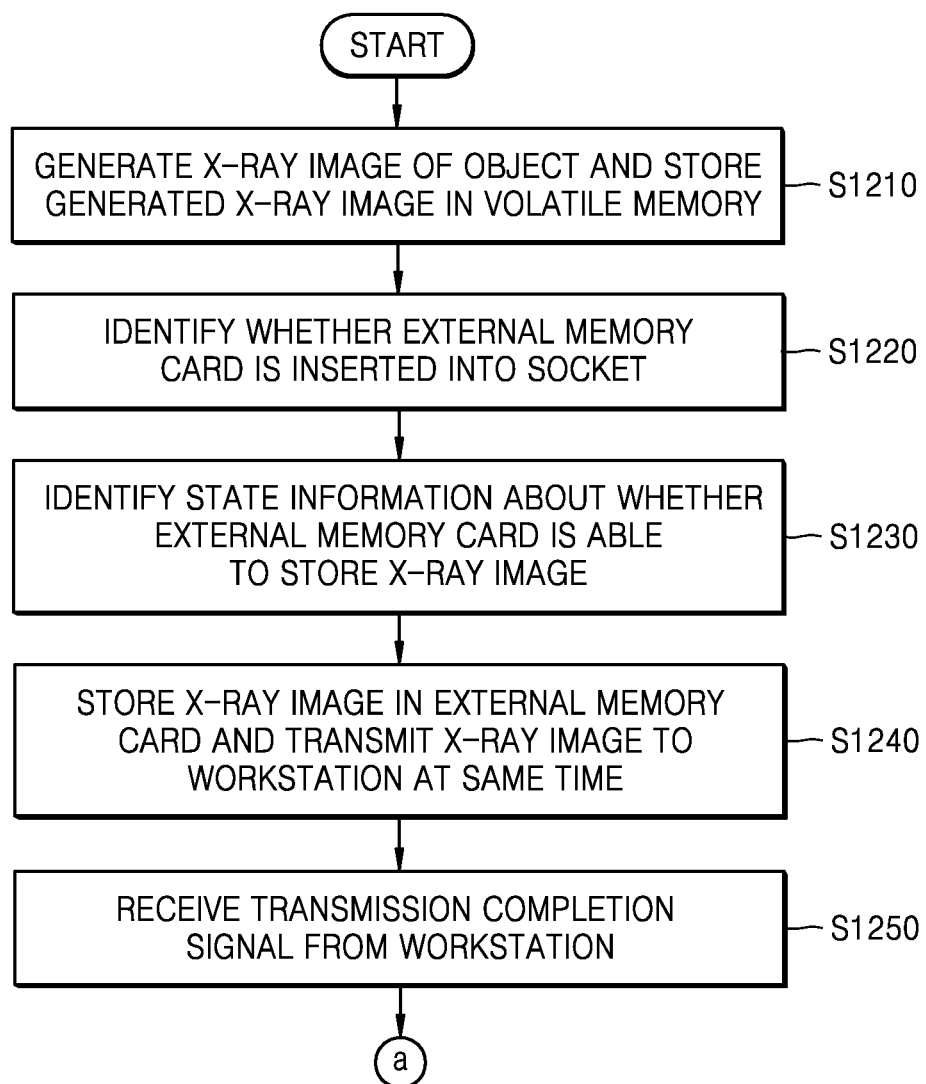
FIG. 12 is a flowchart of a method by which a mobile X-ray detector processes an X-ray image, according to an embodiment.

FIG. 12 is a flowchart of a method by which the mobile X-ray detector 1000 processes an X-ray image according to an embodiment of the disclosure. In FIG. 12, a generated X-ray image is stored in the external memory card 1330, regardless of an exceptional situation due to interruption or cut-off of power supply to the mobile X-ray detector 1000.

In operation S1210, the mobile X-ray detector 1000 generates an X-ray image of an object, and stores the generated X-ray image in a volatile memory. In an embodiment of the disclosure, the mobile X-ray detector 1000 may generate the X-ray image of the object by detecting an X-ray emitted by an X-ray emitter to the object and transmitted through the object. A specific method of generating the X-ray image of the object may be the same as that of FIG. 6, and thus a repeated explanation will be omitted.

The mobile X-ray detector 1000 may temporarily store the generated X-ray image in the volatile memory.

In operation S1220, the mobile X-ray detector 1000 determines whether the external memory card 1330, as shown for example in FIG. 4A, is inserted into the external memory socket 1020, as shown for example in FIG. 4A. The external memory card 1330 may include at least one of, for example, a multimedia card micro type or card type memory, for example an SD memory or an XD memory. The external memory card 1330 may be separated from the external memory socket 1020, when the external memory card 1330 is not normally mounted on the external memory socket 1020 due to its low durability or when the mobile X-ray detector 1000 falls to the floor due to poor manipulation. The processor 1200 may monitor a state of the external memory socket 1020, and may determine whether the external memory card 1330 is appropriately inserted by accessing the external memory card 1330 through the external memory socket 1020.

In operation S1230, the mobile X-ray detector 1000 identifies state information about whether the external memory card 1330 may store the X-ray image. In an embodiment of the disclosure, the processor 1200, as shown for example in FIG. 5, of the mobile X-ray detector 1000 may identify state information including at least one of a card type of the external memory card 1330 inserted into the external memory socket 1020, compatibility information with the mobile X-ray detector 1000, capacity information, or information about whether a write operation is possible. The processor 1200 may determine whether the external memory card 1330 may store the X-ray image based on the identified state information. For example, the processor 1200 may determine whether the external memory card 1330 may store the X-ray image by identifying residual capacity information of the external memory card 1330 and comparing the residual capacity information with a file size of the X-ray image.

In an embodiment of the disclosure, the mobile X-ray detector 1000 may transmit the state information of the external memory card 1330 to a workstation. The workstation may receive the state information, and may display, on a display, information about whether the X-ray image may be stored in the external memory card 1330. A user may determine whether the X-ray image may be stored in the external memory card 1330 and whether the external memory card 1330 needs to be replaced through the information displayed on the display.

In operation S1240, the mobile X-ray detector 1000 stores the X-ray image in the external memory card 1330 and transmits the X-ray image to the workstation at the same time. In an embodiment, at least a portion of the X-ray image may be stored in the external memory card 1330 while at least a portion of the X-ray image is being transmitted to the workstation. In an embodiment of the disclosure, the processor 1200 may control the communicator 1400, as shown for example in FIG. 5, to store at least one X-ray image in the external memory card 1330 and transmit the at least one X-ray image to the workstation at the same time. In operation S1240, unlike in FIG. 11, all of the at least one X-ray image obtained for the object may be stored in the external memory card 1330 regardless of interruption or cut-off of power supply. Also, in operation S1240, unlike in FIG. 11, the at least one X-ray image may be stored and transmitted at the same time. In general, in order to transmit at least one X-ray image to a workstation, a transmission time may be required according to a data communication environment and a delay due to the transmission time may occur. However, because the mobile X-ray detector 1000 according to an embodiment of the disclosure may transmit at least one X-ray image and may store the at least one X-ray image in the external memory card 1330 at the same time, a processing speed may be increased and an unnecessary time delay may be avoided.

In operation S1250, the mobile X-ray detector 1000 receives a transmission completion signal from the workstation.

In related art, a mobile X-ray detector may operate by obtaining an X-ray image of an object, temporarily storing the X-ray image in a volatile memory, and transmitting the stored X-ray image to a workstation. Also, even when the mobile X-ray detector 1000 includes the nonvolatile memory 1320, the nonvolatile memory 1320 generally includes a flash memory or eMMC, and in this case, the number of times an X-ray image may be stored, that is, the number of write cycles, is limited to about 10,000. For example, when a size of one X-ray image obtained when the mobile X-ray detector 1000 images an object is about 20 megabytes and the mobile X-ray detector 1000 obtains 500 X-ray images a day, the mobile X-ray detector 1000 stores, in a flash memory, an image data file of about 10 gigabytes a day. Because the number of write cycles of the flash memory is limited, there is a limitation in storing all X-ray images. Also, when it is impossible to write or read data to or from the flash memory attached to a main board in the mobile X-ray detector 1000, the housing 1010, as shown for example in FIG. 4A, of the mobile X-ray detector 1000 may be removed and related parts may be replaced, which may cause significant monetary damage.

Unlike such an internal flash memory, the external memory card 1330 may be easily replaced, and when a failure or a malfunction occurs, a new external memory card 1330 may be used. Because the mobile X-ray detector 1000 according to an embodiment of the disclosure uses the external memory card 1330, convenience may be improved and monetary damage may be reduced.

However, the external memory card 1330 may have a higher failure rate than the flash memory due to its low durability or the like. In order to solve durability problems, the mobile X-ray detector 1000 according to an embodiment of the disclosure may monitor state information of the external memory card 1330 and may store an X-ray image according to a monitoring result.

Figure 13A:
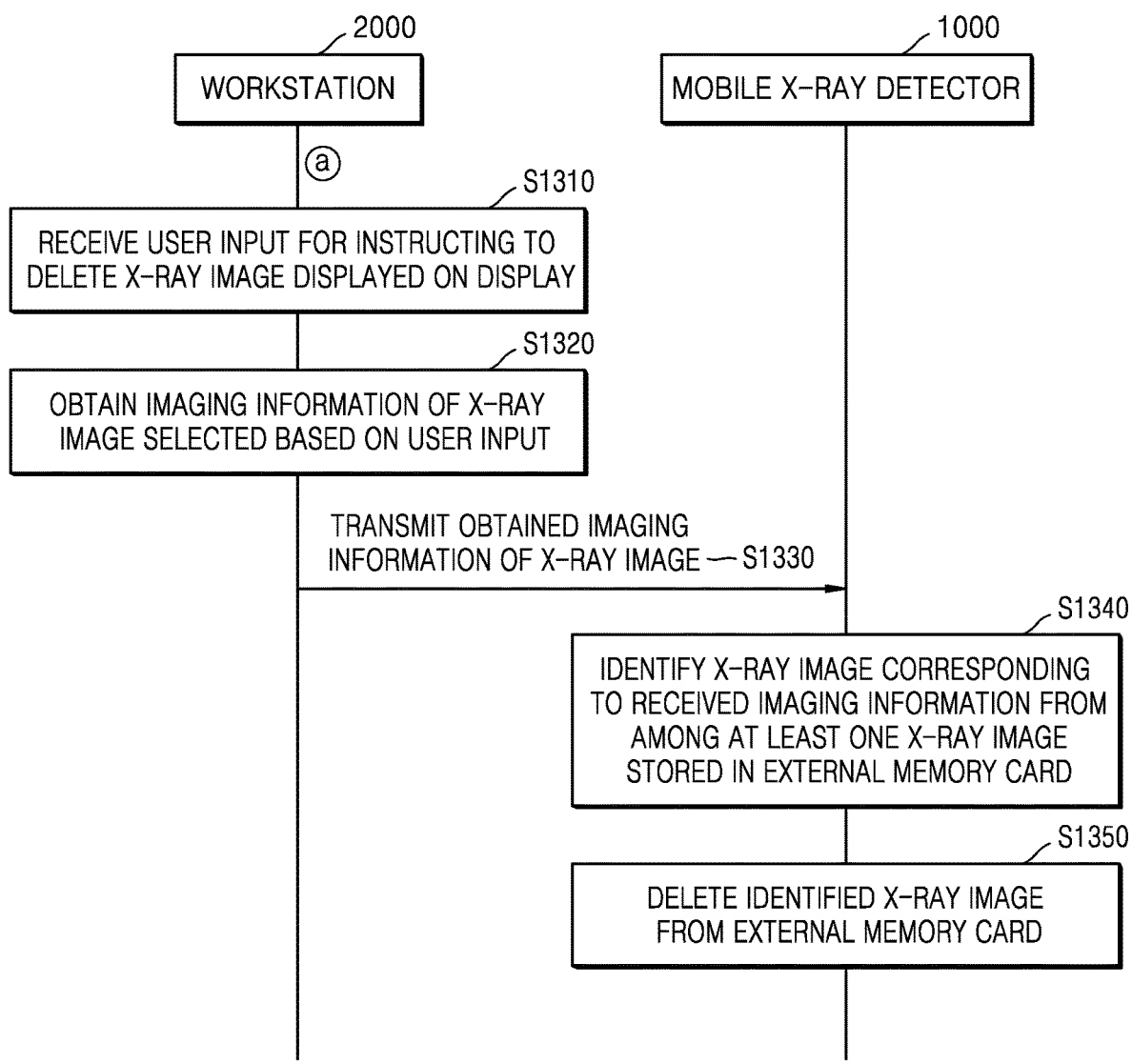
FIG. 13A is a flowchart of a method by which an X-ray imaging apparatus processes an X-ray image stored in an external memory card of the mobile X-ray detector, according to an embodiment.

FIG. 13A is a flowchart of a method by which an X-ray imaging apparatus processes an X-ray image stored in the external memory card 1330, as shown for example in FIG. 4A, of the mobile X-ray detector 1000 according to an embodiment of the disclosure.

In operation S1310, the workstation 2000 receives a user input for instructing to delete an X-ray image displayed on a display. In an embodiment of the disclosure, the workstation 2000 may display at least one X-ray image for which the storage in the external memory card 1330 of the mobile X-ray detector 1000 and the transmission to the workstation 2000 are completed, on the display. A user may select an X-ray image to be deleted from among the at least one X-ray image displayed on the display.

In an embodiment of the disclosure, the workstation 2000 may display at least one thumbnail image respectively corresponding to the at least one X-ray image, on the display. The user may select a thumbnail image corresponding to the X-ray image to be deleted from among the at least one thumbnail image displayed on the display.

In operation S1320, the workstation 2000 obtains imaging information of the X-ray image selected based on the user input. For example, the imaging information may include information about at least one of, for example, patient identification information (patient ID), an imaging protocol, imaging conditions, or an imaging timing.

In operation S1330, the workstation 2000 transmits the obtained imaging information of the X-ray image to the mobile X-ray detector 1000. In an embodiment of the disclosure, the workstation 2000 may transmit the imaging information of the X-ray image to the mobile X-ray detector 1000 by using the communicator 2400, as shown for example in FIG. 14.

In operation S1340, the mobile X-ray detector 1000 identifies an X-ray image corresponding to the received imaging information from among the at least one X-ray image stored in the external memory card 1330. In an embodiment of the disclosure, the processor 1200, as shown for example in FIG. 5, of the mobile X-ray detector 1000 may scan the external memory card 1330, and may obtain imaging information of each of the at least one X-ray image stored in the external memory card 1330. The processor 1200 may identify an X-ray image having the same imaging information as the imaging information received from the workstation 2000 from among the obtained imaging information of the at least one X-ray image.

In operation S1350, the mobile X-ray detector 1000 deletes the identified X-ray image from the external memory card 1330.

Figure 13B:
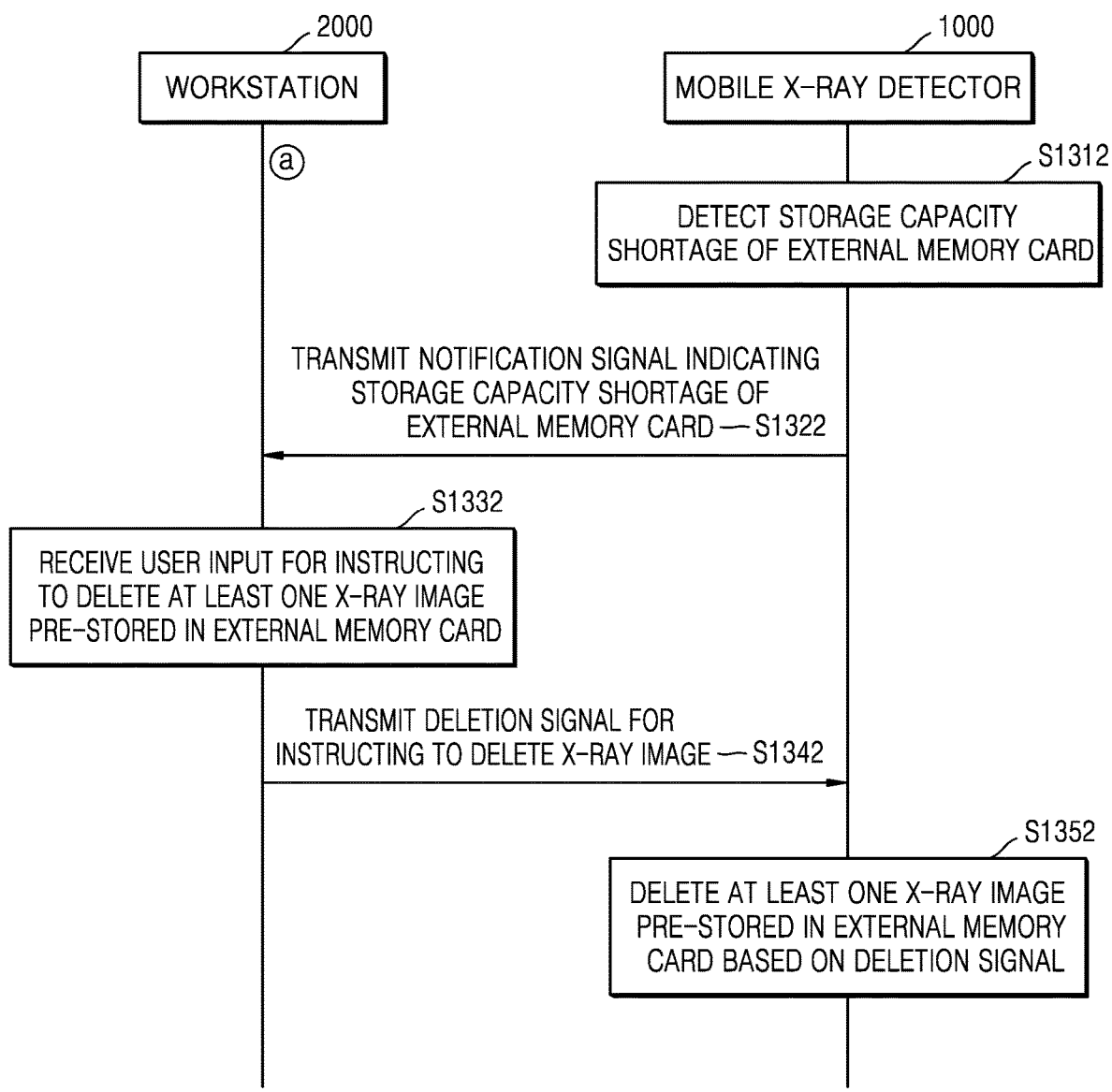
FIG. 13B is a flowchart of a method by which an X-ray imaging apparatus processes an X-ray image stored in an external memory card of a mobile X-ray detector, according to an embodiment.

FIG. 13B is a flowchart of a method by which an X-ray imaging apparatus processes an X-ray image stored in the external memory card 1330, as shown for example in FIG.

4A, of the mobile X-ray detector 1000 according to an embodiment of the disclosure.

In operation S1312, the mobile X-ray detector 1000 detects a storage capacity shortage of the external memory card 1330. In an embodiment of the disclosure, the processor 1200, as shown for example in FIG. 5, of the mobile X-ray detector 1000 may identify size information of a stored file and residual capacity information by scanning the external memory card 1330. The processor 1200 may compare a residual capacity of the external memory card 1330 with a size of one X-ray image and may determine whether the residual capacity of the external memory card 1330 is unable to store the X-ray image. For example, a size of one X-ray image may be, but is not limited to, about 20 megabytes.

In operation S1322, the mobile X-ray detector 1000 transmits a notification signal indicating a storage capacity shortage of the external memory card 1330, to the workstation 180.

In operation S1332, the workstation 2000 receives a user input for instructing to delete at least one X-ray image pre-stored in the external memory card 1330. In an embodiment of the disclosure, the workstation 2000 may display the at least one X-ray image pre-stored in the external memory card 1330 on a display.

In an embodiment of the disclosure, the workstation 2000 may receive a user input for instructing to delete all of the at least one X-ray image displayed on the display. In another embodiment of the disclosure, the workstation 2000 may receive a user input for selecting one or more from among the at least one X-ray image displayed on the display.

In operation S1342, the workstation 2000 transmits a deletion signal for instructing to delete the X-ray image to the mobile X-ray detector 1000. In an embodiment of the disclosure, the workstation 2000 may transmit imaging information corresponding to the X-ray image instructed to be deleted to the mobile X-ray detector 1000.

In operation S1352, the mobile X-ray detector 1000 deletes the at least one X-ray image pre-stored in the external memory card 1330 based on the deletion signal. In an embodiment of the disclosure, the processor 1200 may identify an X-ray image corresponding to the imaging information from among the at least one X-ray image pre-stored in the external memory card 1330 based on the imaging information of the X-ray image to be deleted obtained from the workstation 2000, and may delete the identified X-ray image. In an embodiment of the disclosure, when an instruction to delete all of the at least one X-ray image pre-stored in the external memory card 1330 is received from the workstation 2000, the processor 1200 may delete all of the at least one X-ray image pre-stored in the external memory card 1330.

In FIGS. 13A and 13B, because the mobile X-ray detector 1000 deletes the X-ray image identified by the user from among the at least one X-ray image pre-stored in the external memory card 1330, capacity problems of the external memory card 1330 may be solved.

Figure 14:
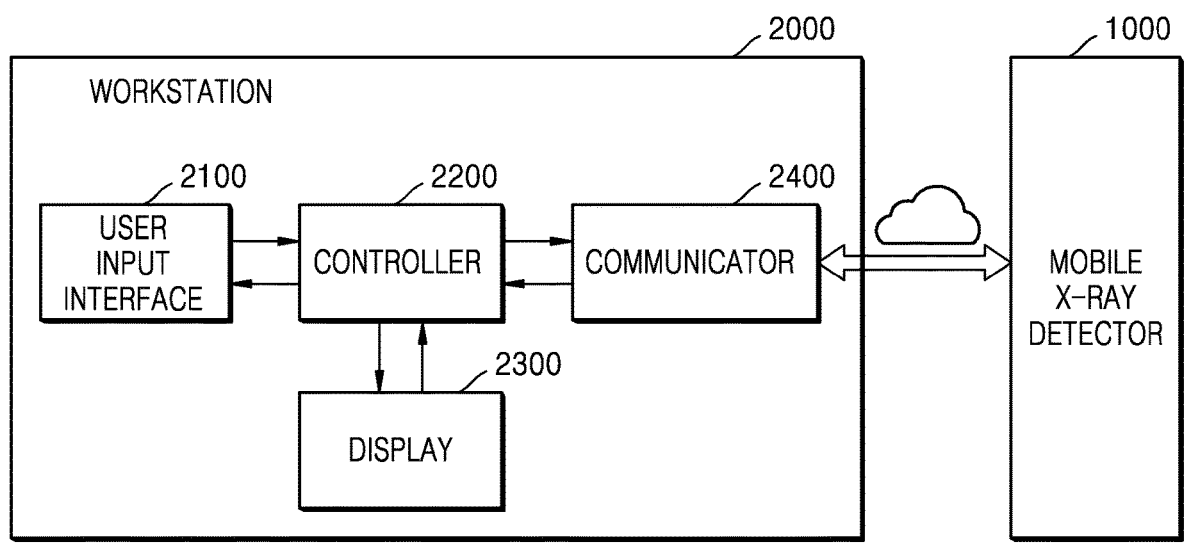
FIG. 14 is a block diagram illustrating examples of elements of a workstation according to an embodiment.

FIG. 14 is a block diagram illustrating elements of the workstation 2000 according to an embodiment of the disclosure.

The workstation 2000 may receive a command or the like from a user, and may transmit a control signal for controlling an X-ray emitter and the mobile X-ray detector 1000 to the X-ray emitter and the mobile X-ray detector 1000 based on the received command of the user.

Referring to FIG. 14, the workstation 2000 may include the user input interface 2100, the controller 2200, the display 2300, and the communicator 2400.

The user input interface 2100 may receive a user input that manipulates the X-ray emitter and the mobile X-ray detector 1000, obtains an X-ray image, or processes the obtained X-ray image. The user input interface 2100 may include a hardware element such as, but not limited to, a button, a key pad, a mouse, a track ball, a touchpad, a touchscreen, or a jog switch. When the display 2300 includes a touchscreen, the user input interface 2100 may be integrated with the touchscreen and may receive a touch input of the user.

In an embodiment of the disclosure, the user input interface 2100 may receive a user input selecting one of at least one user interface displayed on the display 2300. In an embodiment of the disclosure, the user input interface 2100 may receive a user input selecting one of a plurality of thumbnail images displayed on the display 2300.

The controller 2200 may control functions or operations of the user input interface 2100, the display 2300, and the communicator 2400.

The controller 2200 may include a processor and a memory. In an embodiment of the disclosure, the controller 2200 may include a memory that stores program code and data for performing a certain function, and a processor that processes the program code and the data stored in the memory. In an embodiment of the disclosure, the controller 2200 may be implemented in any of various combinations of one or more memories and one or more processors. The processor may generate and delete a program module according to an operation state of the workstation 2000, and may process operations of the program module.

The processor of the controller 2200 may be implemented as a hardware device having a computing capability for general-purpose image processing. For example, the processor of the controller 2200 may include a hardware module including at least one of a central processing unit (CPU), a microprocessor, or a graphics processing unit (GPU).

The memory that is a hardware device for storing program code or data for performing each function of the workstation 2000 may include, but is not limited to, a random-access memory (RAM) or a read-only memory (ROM).

The display 2300 may display a screen image for guiding a user input, an X-ray image, and a screen image showing state information of an X-ray imaging apparatus. In an embodiment of the disclosure, the display 2300 may display an X-ray image or a thumbnail image of the X-ray image under the control of the controller 2200. The display 2300 may be a passive device operating under the control of the controller 2200. The display 2300 may include a physical device including at least one of, for example, but not limited to, a liquid-crystal display (LCD), a plasma display panel (PDP) display, an organic light-emitting (OLED) display, a field-emission display (FED), a light-emitting diode (LED) display, a vacuum fluorescent display (VFD) display, a digital light processing (DLP) display, a flat-panel display, a three-dimensional (3D) display, or a transparent display. In an embodiment of the disclosure, the display 2300 may include a touchscreen including a touch interface.

The communicator 2400 may be connected to an external device, for example an external server, a medical device, or a portable terminal, for example a smartphone, a tablet PC, or a wearable device, and may transmit or receive data. In an embodiment of the disclosure, the communicator 2400 may perform data communication by using a wired or wireless communication method with the mobile X-ray detector 1000.

In an embodiment of the disclosure, the communicator 2400 may receive a control signal from the external device, may transmit the received control signal to the controller 2200, and may control the controller 120 to control the X-ray imaging apparatus according to the received control signal. Also, the controller 2200 may transmit a control signal to the external device through the communicator 2400 and may control the external device according to the control signal of the controller 2200. For example, the external device may process data of the external device according to a control signal of the controller 2200 received through the communicator 2400.

The communicator 2400 may include one or more elements for communication with the external device. The communicator 2400 may perform data communication with the mobile X-ray detector 1000 by using at least one of data communication methods including wired LAN, wireless LAN, Wi-Fi, Bluetooth, Zigbee, WFD, IrDA, BLE, NFC, Wibro, WiMAX, SWAP, WiGig, and RF communication.

In an embodiment of the disclosure, the controller 2200 may control the display 2300 to display, on the display 2300, at least one user interface (UI) indicating imaging information of at least one non-transmitted X-ray image that is not transmitted to the workstation 2000 or whose transmission to the workstation 2000 is stopped from among at least one X-ray image generated by the mobile X-ray detector 1000 and stored in the nonvolatile memory 1320, as shown for example in FIG. 5. The imaging information may include patient identification information, for example patient id, and imaging protocol information of each of the at least one non-transmitted X-ray image.

In an embodiment of the disclosure, the user input interface 2100 may receive a user input selecting one of at least one user interface displayed on the display 2300. The user input interface 2100 may provide a signal for the user input to the controller 2200. In an embodiment of the disclosure, the controller 2200 may transmit a query signal for requesting to transmit an X-ray image corresponding to the user interface selected according to the received user input and imaging information of the X-ray image, to the mobile X-ray detector 1000 through the communicator 2400.

The controller 2200 may obtain the X-ray image corresponding to the imaging information from among the at least one non-transmitted X-ray image stored in the nonvolatile memory 1320 of the mobile X-ray detector 1000, from the mobile X-ray detector 1000 through the communicator 2400. In an embodiment of the disclosure, the controller 2200 may control the display 2300 to display the obtained X-ray image on the display 2300.

In an embodiment of the disclosure, the controller 2200 may receive imaging information of each of a plurality of X-ray images generated by the mobile X-ray detector 1000 and information about transmission, from the mobile X-ray detector 1000 through the communicator 2400. The information about transmission may include information about whether transmission of the X-ray image is completed, the X-ray image is not transmitted, or X-ray image is stopped from being transmitted to the workstation 2000 from among the plurality of X-ray images.

In an embodiment of the disclosure, as the controller 2200 receives the imaging information of each of the plurality of X-ray images and the information about transmission, the controller 2200 may control the communicator 2400 to transmit a signal for requesting to transmit a plurality of thumbnail images of the plurality of X-ray images to the mobile X-ray detector 1000. The controller 2200 may obtain the plurality of thumbnail images from the mobile X-ray detector 1000 through the communicator 2400.

In an embodiment of the disclosure, the controller 2200 may control the display 2300 to display the obtained plurality of thumbnail images on the display 2300. The controller 2200 may select one of the plurality of thumbnail images based on a user input received through the user input interface 2100. The controller 2200 may control the communicator 2400 to transmit, to the mobile X-ray detector 1000, a signal for requesting to transmit a first X-ray image corresponding to the selected thumbnail image from among the plurality of X-ray images. The controller 2200 may obtain the first X-ray image from the mobile X-ray detector 1000, through the communicator 2400.

Figure 15:
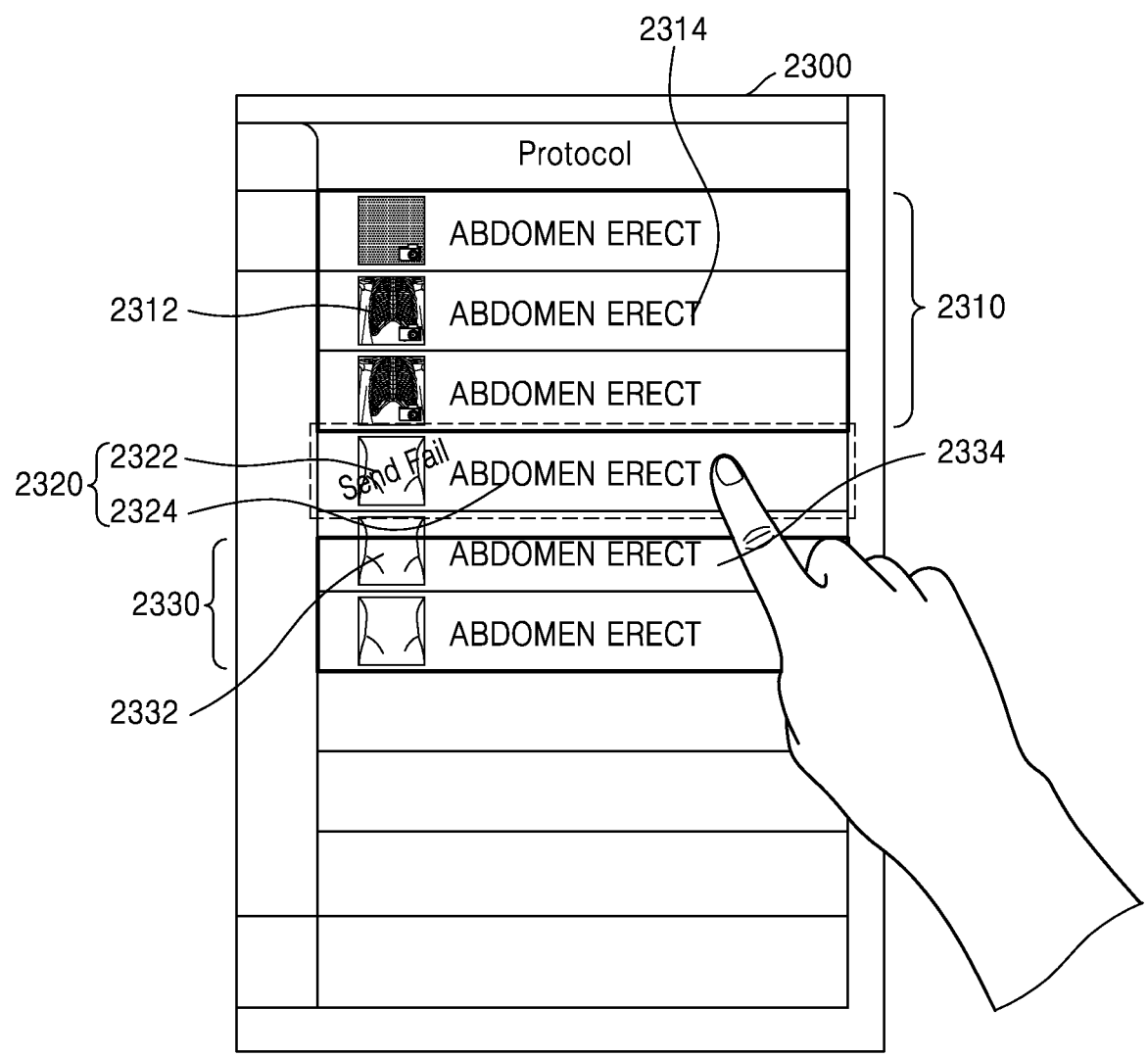
FIG. 15 is a diagram of a user interface (UI) displayed on a display of a workstation, according to an embodiment.

FIG. 15 is a diagram of a user interface displayed on the display 2300 of the workstation 2000 according to an embodiment of the disclosure.

Referring to FIG. 15, the display 2300 of the workstation 2000 may display a user interface for an X-ray image of an object obtained by the mobile X-ray detector 1000. The user interface may include protocol information of the X-ray image and an imaging portion.

In an embodiment of the disclosure, the display 2300 may display a first user interface (UI) 2310 indicating an X-ray image that is completed being obtained by the mobile X-ray detector 1000 and transmitted to the workstation 2000 and imaging protocol information of the X-ray image, a second UI 2320 indicating imaging protocol information of an X-ray image that is obtained by the mobile X-ray detector 1000 but is not transmitted to the workstation 2000, and a third UI 2330 indicating imaging protocol information of an X-ray image that is not obtained by the mobile X-ray detector 1000.

The first UI 2310 may include an image 2312 of the X-ray image that is completed being obtained and transmitted and imaging protocol information 2314 of the X-ray image. The image 2312 included in the first UI 2310 may be, but is not limited to, the X-ray image received from the mobile X-ray detector 1000. In an embodiment of the disclosure, the image 2312 may be a thumbnail image of the X-ray image. The imaging protocol information 2314 may include at least one of an imaging target portion, a position or a posture of the mobile X-ray detector 1000 during imaging, or patient ID information. The imaging protocol information 2314 may be displayed using characters or a symbol.

The second UI 2320 may include a non-transmission UI 2322 and imaging protocol information 2324 indicating that transmission of the X-ray image is stopped or failed. The non-transmission UI 2322 may include an image of an imaging target portion and at least one indicator from among characters, a symbol, a display, a color, or a pattern indicating a non-transmission state. In an embodiment of the disclosure, the non-transmission UI 2322 may overlay text, e.g., 'Send Fail', for notifying that the X-ray image is not transmitted on the image of the imaging target portion. However, the disclosure is not limited thereto, and the non-transmission UI 2322 may display any other type of text or indicator such as an 'X' on the image of the imaging target portion, or may display the image of the imaging target portion in a color, e.g., a red color, to be distinguished from the image 2312 of the first UI 2310.

The third UI 2330 may include an image 2332 of the X-ray image that is not obtained and imaging protocol information 2334. The image 2332 may be an image of a portion to be imaged. When the X-ray image is completed being obtained by the mobile X-ray detector 1000 and transmitted to the workstation 2000, the image 2332 may be changed to the obtained X-ray image or a thumbnail image of the obtained X-ray image.

A user may identify the non-transmission UI 2322 displayed on the display 2300, and may obtain imaging protocol information corresponding to a non-transmitted X-ray image through the imaging protocol information 2324. The user input interface 2100 may receive a user input selecting the non-transmission UI 2322 of the second UI 2320. Although the user input is a touch input in FIG. 15 for convenience of explanation, the user input is not limited to the touch input.

The controller 2200, as shown for example in FIG. 14, may control the communicator 2400 to transmit, to the mobile X-ray detector 1000, a request signal for requesting to transmit the non-transmitted X-ray image displayed on the non-transmission UI 2322 based on the user input obtained from the user input interface 2100.

Figure 16:
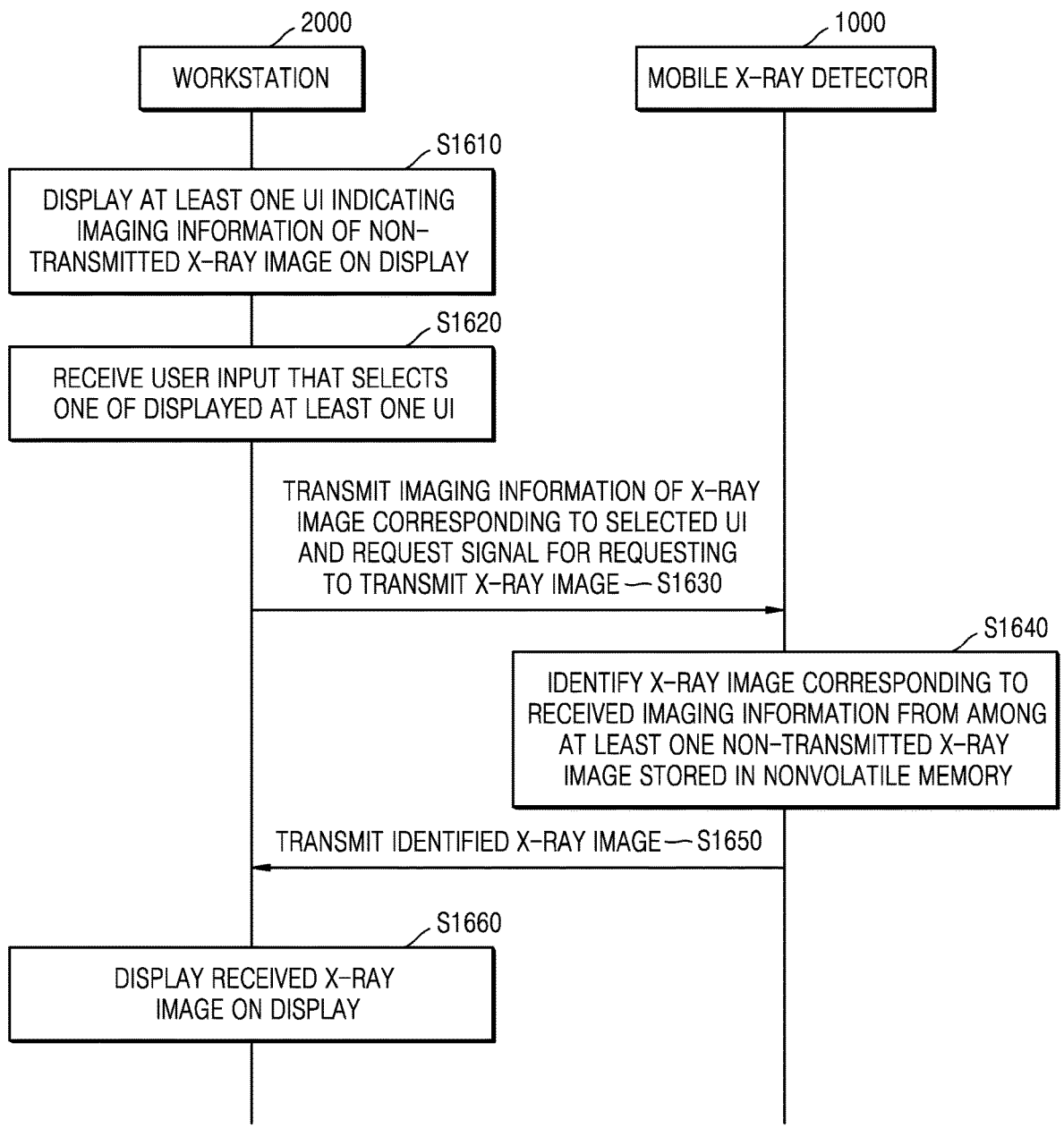
FIG. 16 is a flowchart of a method by which an X-ray imaging apparatus obtains a non-transmitted X-ray image from the mobile X-ray detector and displays the obtained X-ray image, according to an embodiment.

FIG. 16 is a flowchart of a method by which an X-ray imaging apparatus obtains a non-transmitted X-ray image from the mobile X-ray detector 1000 and displays the obtained non-transmitted X-ray image according to an embodiment of the disclosure.

In operation S1610, the workstation 2000 displays at least one UI indicating imaging information of a non-transmitted X-ray image on the display 2300, as shown for example in FIG. 14. In an embodiment of the disclosure, the at least one UI may include at least one of an imaging target portion of the non-transmitted X-ray image, a position or posture of the mobile X-ray detector 1000 during imaging, or patient ID information.

In an embodiment of the disclosure, the at least one UI may include an image of the imaging target portion and at least one indicator from among characters, a symbol, a display, a color, or a pattern indicating a non-transmission state. In an embodiment of the disclosure, the at least one UI may overlay text, e.g., 'Send Fail', for notifying that an X-ray is not transmitted on the image of the imaging target portion. However, the disclosure is not limited thereto, and the at least one UI may display 'X' on the image of the imaging target portion or may display the image of the imaging target portion in a color, e.g., a red color, to be distinguished from a UI indicating an X-ray image whose transmission is completed.

In operation S1620, the workstation 2000 receives a user input selecting one of the displayed at least one UI.

In operation S1630, the workstation 2000 transmits, to the mobile X-ray detector 1000, imaging information of an X-ray image corresponding to the selected UI and a request signal for requesting to transmit the X-ray image.

In operation S1640, the mobile X-ray detector 1000 identifies an X-ray image corresponding to the received imaging information from among at least one non-transmitted X-ray image stored in the nonvolatile memory 1320, as shown for example in FIG. 5. The processor 1200, as shown for example in FIG. 5, of the mobile X-ray detector 1000 may scan the nonvolatile memory 1320 and may obtain imaging information of each of the at least one non-transmitted X-ray image stored in the nonvolatile memory 1320. The processor 1200 may identify an X-ray image having the same imaging information as the imaging information received from the workstation 2000 from among the obtained imaging information of the at least one X-ray image.

In operation S1650, the mobile X-ray detector 1000 transmits the identified X-ray image to the workstation 2000.

In operation S1660, the workstation 2000 displays the received X-ray image on the display 2300.

Figure 17:
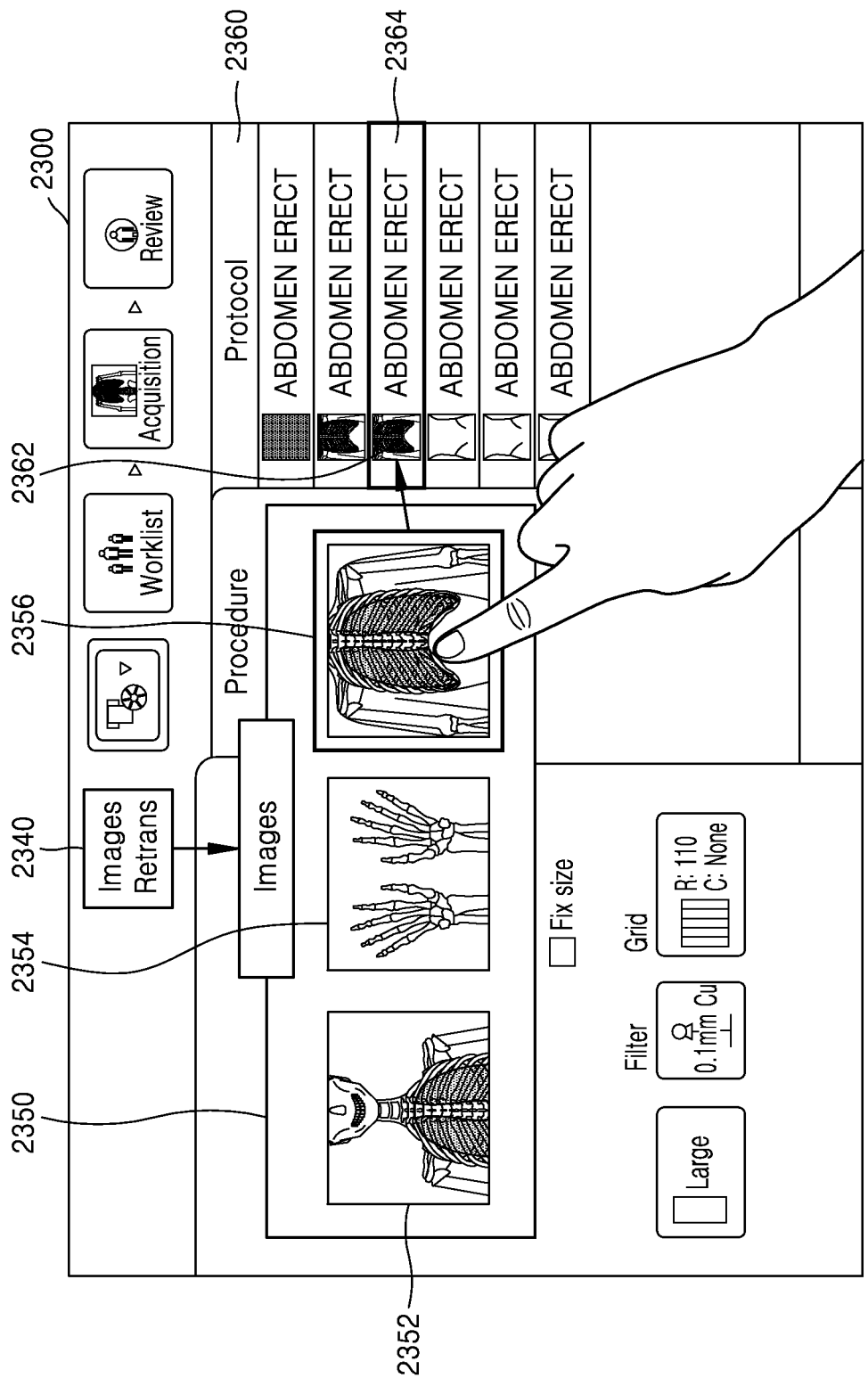
FIG. 17 is a diagram of a UI displayed on the display of the workstation, according to an embodiment.

FIG. 17 is a diagram of a user interface displayed on the display 2300 of the workstation 2000 according to an embodiment of the disclosure.

Referring to FIG. 17, the workstation 2000 may detect a non-transmitted X-ray image whose transmission is stopped or failed from the mobile X-ray detector 1000, and may display a retransmission UI 2340 related to retransmission of the detected non-transmitted X-ray image on the display 2300. The retransmission UI 2340 may be displayed on the display 2300 only when the non-transmitted X-ray image is detected from the mobile X-ray detector 1000.

When the user input interface 2100, as shown for example in FIG. 14, receives a user input selecting the retransmission UI 2340, the controller 2200, as shown for example in FIG. 14, may control the communicator 2400, as shown for example in FIG. 14, to transmit, to the mobile X-ray detector 1000, a request signal for requesting to transmit a thumbnail image of the non-transmitted X-ray image. The controller 2200 may obtain a plurality of thumbnail images, e.g., first through third thumbnail images 2352, 2354, and 2356, of a plurality of non-transmitted X-ray images through the communicator 2400, and may display the obtained first through third thumbnail images 2352, 2354, and 2356 on the display 2300.

The user input interface 2100 may receive a user input selecting the third thumbnail image 2356 from among the first through third thumbnail images 2352, 2354, and 2356 displayed on the display 2300. The controller 2200 may select the third thumbnail image 2356 based on the user input received through the user input interface 2100, and may control the display 2300 to display third imaging protocol information 2364 corresponding to the third thumbnail image 2356 from among imaging protocol information included in a work list 2360 to be distinguished from other imaging protocol information.

The user input interface 2100 may receive a user input selecting the third imaging protocol information 2364. The controller 2200 may control the communicator 2400, as shown for example in FIG. 14, to transmit, to the mobile X-ray detector 1000, a request signal for requesting to transmit an X-ray image corresponding to the third imaging protocol information 2364 selected based on the user input. In an embodiment of the disclosure, the controller 2200 may receive the X-ray image corresponding to the third imaging protocol information 2364 from the mobile X-ray detector 1000 through the communicator 2400, and may control the display 2300 to display the X-ray image on the work list 2360.

In an embodiment of the disclosure, when the controller 2200 receives the X-ray image from the mobile X-ray detector 1000, the controller 2200 may transmit a deletion signal for instructing to delete the X-ray image for which transmission through the communicator 2400 to the mobile X-ray detector 1000 is completed.

Figure 18:
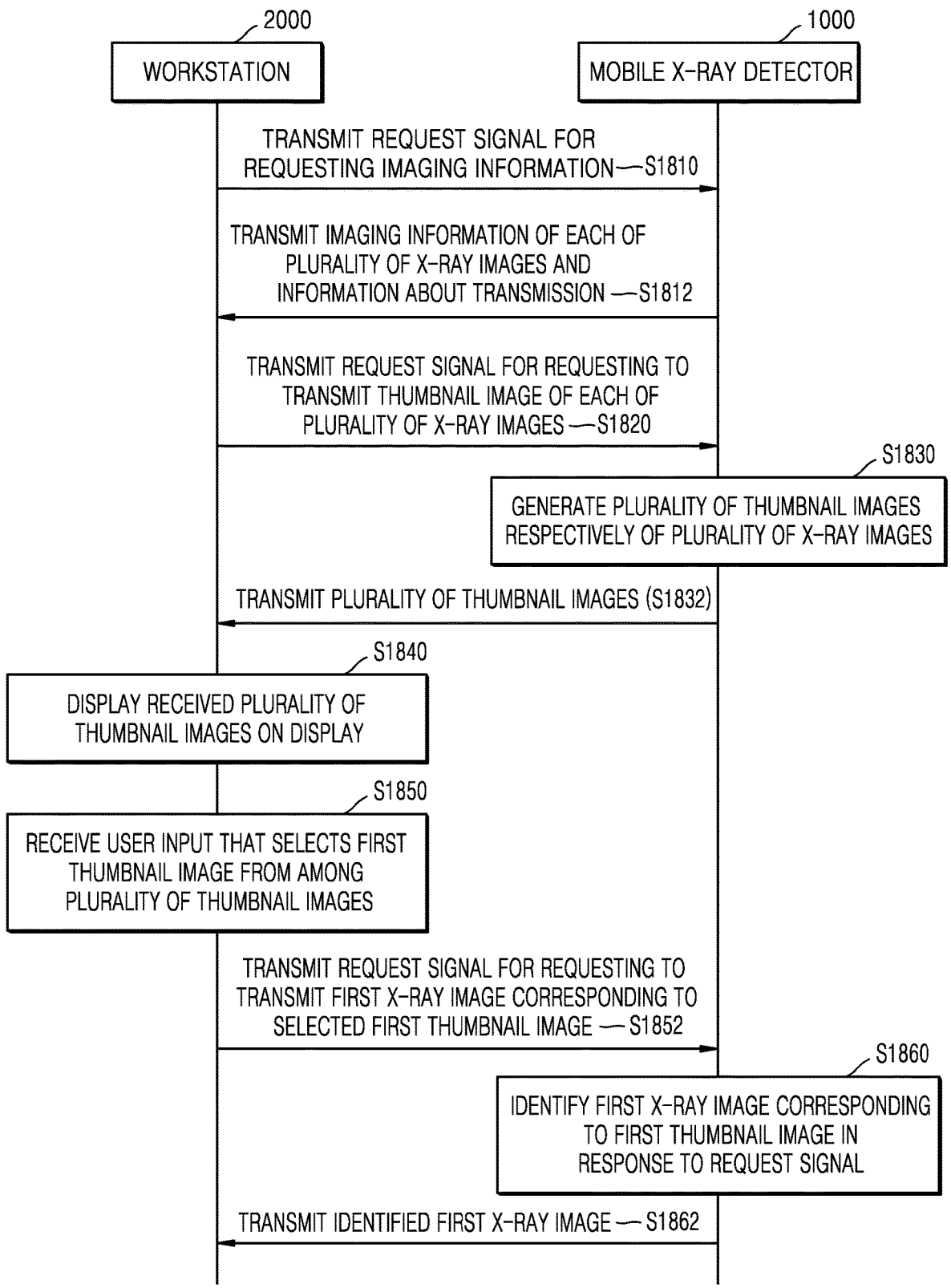
FIG. 18 is a flowchart of a method by which an X-ray imaging apparatus obtains an X-ray image from the mobile X-ray detector, according to an embodiment.

FIG. 18 is a flowchart of a method by which an X-ray imaging apparatus obtains an X-ray image from the mobile X-ray detector 1000 according to an embodiment of the disclosure.

In operation S1810, the workstation 2000 transmits a request signal for requesting imaging information of each of a plurality of X-ray images stored in the mobile X-ray detector 1000. In an embodiment of the disclosure, when the workstation 2000 detects a non-transmitted X-ray image for which transmission is stopped or failed from the mobile X-ray detector 1000, the workstation 2000 may display the retransmission UI 2340, as shown for example in FIG. 17, on the display 2300, as shown for example in FIG. 14, and when the workstation 2000 receives a user input selecting the displayed retransmission UI 2340, the workstation 2000 may transmit, to the mobile X-ray detector 1000, a request signal for requesting to transmit the non-transmitted X-ray image.

In operation S1812, the mobile X-ray detector 1000 transmits, to the workstation 2000, the imaging information of each of the plurality of X-ray images and information about transmission. In an embodiment of the disclosure, the mobile X-ray detector 1000 may transmit, to the workstation 2000, information about whether each of the plurality of X-ray images stored in the nonvolatile memory 1320 has completed transmission, is not transmitted, or has been stopped from being transmitted.

In operation S1820, the workstation 2000 transmits, to the mobile X-ray detector 1000, a request signal for requesting to transmit a thumbnail image of each of the plurality of X-ray images.

In operation S1830, the mobile X-ray detector 1000 generates a plurality of thumbnail images of the plurality of X-ray images in response to the request signal received from the workstation 2000.

In operation S1832, the mobile X-ray detector 1000 transmits the plurality of thumbnail images to the workstation 2000.

In operation S1840, the workstation 2000 displays the received plurality of thumbnail images on the display 2300, as shown for example in FIG. 14.

In operation S1850, the workstation 2000 receives a user input selecting a first thumbnail image from among the plurality of thumbnail images. In an embodiment of the disclosure, the workstation 2000 may receive a user input selecting the first thumbnail image from among the displayed plurality of thumbnail images through the user input interface 2100, as shown for example in FIG. 14, and may display first imaging protocol information of the first thumbnail image selected based on the received user input to be distinguished from other imaging protocol information.

In operation S1852, the workstation 2000 transmits, to the mobile X-ray detector 1000, a request signal for requesting transmission of a first X-ray image corresponding to the selected first thumbnail image. In an embodiment of the disclosure, the workstation 2000 may transmit, to the mobile X-ray detector 1000, imaging information of the first X-ray image corresponding to the first thumbnail image along with the request signal.

In operation S1860, the mobile X-ray detector 1000 identifies the first X-ray image corresponding to the first thumbnail image in response to the request signal received from the workstation 2000. In an embodiment of the disclosure, the processor 1200, as shown for example in FIG. 5, of the mobile X-ray detector 1000 may scan the nonvolatile memory 1320, as shown for example in FIG. 5, may obtain imaging information of each of the plurality of X-ray images stored in the nonvolatile memory 1320, and may identify the first X-ray image having the same imaging information as the imaging information received from the workstation 2000 from among the obtained imaging information of the plurality of X-ray images.

In operation S1862, the mobile X-ray detector 1000 transmits the identified first X-ray image to the workstation 2000.

Embodiments of the disclosure may be implemented as a software program including instructions stored in a computer-readable storage medium.

A computer which is an apparatus capable of calling stored instructions from a storage medium and operating according to an embodiment of the disclosure according to the called instructions may include an X-ray imaging apparatus according to embodiments of the disclosure.

The computer-readable storage medium may be provided as a non-transitory storage medium. Here, 'non-transitory' means that the storage medium does not include a signal and is tangible, but does not distinguish whether data is stored semi-permanently or temporarily in the storage medium.

In addition, a mobile X-ray detector, an X-ray imaging apparatus, and an operating method of the mobile X-ray detector and the X-ray imaging apparatus according to embodiments of the disclosure may be provided in a computer program product. The computer program product may be traded between a seller and a purchaser as a product.

The computer program product may include a software program and a computer-readable storage medium storing the software program. For example, the computer program product may include a product, for example a downloadable application, that is electronically distributed as a software program through an electronic market, for example Google Play Store or AppStore, or a manufacturer of an X-ray imaging apparatus. For electronic distribution, at least a part of the software program may be stored in a storage medium or may be temporarily generated. In this case, the storage medium may be a storage medium of a server of the manufacturer, a server of the electronic market, or a relay server that temporarily stores the software program.

The computer program product may include a storage medium of a server or a storage medium of a device in a system including the server and the device. In embodiments, when a third apparatus, for example a smartphone, communicating with the server or the device exists, the computer program product may include a storage medium of the third apparatus. In embodiments, the computer program product may include a software program itself transmitted from the server to the device or the third apparatus or from the third apparatus to the device.

In this case, one from among the server, the device, and the third apparatus may execute the computer program product and may perform a method according to embodiments of the disclosure. In embodiments, two or more from among the server, the device, and the third apparatus may execute the computer program product and may perform the method according to embodiments of the disclosure.

For example, the server, for example a cloud server or an artificial intelligence (AI) server, may execute the computer program product stored in the server and may control the device communicating with the server to perform the method according to embodiments of the disclosure.

In embodiments, the third apparatus may execute the computer program product and may control the device communicating with the third apparatus to perform the method according to embodiments of the disclosure.

When the third apparatus executes the computer program product, the third apparatus may download the computer program product from the server and may execute the downloaded computer program product. In embodiments, the third apparatus may execute the computer program product that is preloaded and may perform the method according to embodiments of the disclosure.

Embodiments of the disclosure may be implemented on computer-readable recording media storing instructions and data executable by computers. The instructions may be stored as program code, and when being executed by a processor, may cause a certain program module to be generated and a certain operation to be performed. Also, when executed by the processor, the instructions may cause certain operations of embodiments of the disclosure to be performed.

Embodiments of the disclosure have been particularly shown and described with reference to the accompanying drawings. It will be understood by one of ordinary skill in the art that various changes in form and details may be made therein without departing from the spirit and scope of the disclosure as defined by the appended claims. The embodiments of the disclosure should be considered in descriptive sense only and not for purposes of limitation.

What is claimed is:

1. An X-ray imaging apparatus comprising:
a mobile X-ray detector;
a display;
a user input interface;
a communication interface configured to transmit or receive data with the mobile X-ray detector; and
at least one processor configured to:
receive, through the user input interface, a user input for selecting an X-ray image from among at least one non-transmitted X-ray image generated by the mobile X-ray detector,
select, by the received user input, the X-ray image from among the at least one non-transmitted X-ray image,
control the communication interface to transmit, to the mobile X-ray detector, imaging information of the selected X-ray image and a request signal for requesting transmission of the selected X-ray image,
receive, by the communication interface, the X-ray image from the mobile X-ray detector, and
control the display to display the received X-ray image on the display.

2. The X-ray imaging apparatus of claim 1, wherein the at least one processor is further configured to:
control the display to display user interfaces (UIs) indicating imaging information of the at least one non-transmitted X-ray image from among a plurality of X-ray images generated by the mobile X-ray detector, and
control the user input interface to receive a user input selecting UI from the displayed UIs.

3. The X-ray imaging apparatus of claim 2, wherein the at least one processor is further configured to:
detect at least one non-transmitted X-ray image that is not transmitted or whose transmission is stopped from the mobile X-ray detector, and
in response to the at least one non-transmitted X-ray image being detected, control the display to display the UIs on the display.

4. The X-ray imaging apparatus of claim 1, wherein the UIs comprises at least one of imaging target portion of the at least one non-transmitted X-ray image, a position or posture of the mobile X-ray detector during imaging, or patient identification information.

5. The X-ray imaging apparatus of claim 1, wherein the at least one processor is further configured to:
control the communication interface to obtain, from the mobile X-ray detector, at least one thumbnail image of the at least one non-transmitted X-ray image,
control the display to display the at least one thumbnail image on the display, and
receive, through the user input interface, a user input for selecting a thumbnail image from among the displayed at least one thumbnail image.

6. The X-ray imaging apparatus of claim 5, wherein the at least one processor is further configured to control the communication interface to transmit, to the mobile X-ray detector, the request signal for requesting to transmit the X-ray image corresponding to the selected thumbnail image by the received user input.

7. The X-ray imaging apparatus of claim 1, wherein the imaging information comprises patient identification information and imaging protocol information of the at least one non-transmitted X-ray image.

8. The X-ray imaging apparatus of claim 1, wherein the mobile X-ray detector is configured to:
identify the X-ray image based on the received imaging information from among the at least one non-transmitted X-ray image stored in a nonvolatile memory in response to the request signal being received, and
transmit the identified X-ray image to the communication interface.

9. A method, performed by an X-ray imaging apparatus, of processing X-ray images, the method comprising:
receiving a user input for selecting an X-ray image from among at least one non-transmitted X-ray image generated by a mobile X-ray detector;
selecting, by the received user input, the X-ray image from among the at least one non-transmitted X-ray image;
transmitting, to the mobile X-ray detector, imaging information of the selected X-ray image and a request signal for requesting transmission of the selected X-ray image;
receiving the X-ray image from the mobile X-ray detector; and
displaying the received X-ray image.

10. The method of claim 9 further comprises:
displaying user interfaces (UIs) indicating imaging information of the at least one non-transmitted X-ray image from among a plurality of X-ray images generated by the mobile X-ray detector, and
wherein the receiving of the user input comprises receiving a user input selecting UI from the displayed UIs.

11. The method of claim 10, wherein the displaying of the UIs comprises:
detecting at least one non-transmitted X-ray image that is not transmitted or whose transmission is stopped from the mobile X-ray detector; and
in response to the at least one non-transmitted X-ray image being detected, displaying the UIs on the display of the X-ray imaging apparatus.

12. The method of claim 9, wherein the UIs comprise at least one of imaging target portion of the at least one non-transmitted X-ray image, a position or posture of the mobile X-ray detector during imaging, or patient identification information.

13. The method of claim 9, further comprising:
obtaining, from the mobile X-ray detector, at least one thumbnail image of the at least one non-transmitted X-ray image;
displaying the at least one thumbnail image on the display of the X-ray imaging apparatus; and
receiving a user input for selecting a thumbnail image from among the displayed at least one thumbnail image.

14. The method of claim 13, further comprising:
transmitting, to the mobile X-ray detector, the request signal for requesting to transmit the X-ray image corresponding to the selected thumbnail image by the received user input.

15. The method of claim 9, wherein the imaging information comprises patient identification information and imaging protocol information of the at least one non-transmitted X-ray image.

16. An X-ray imaging apparatus comprising:
a mobile X-ray detector;
a display;
a user input interface;
a communication interface configured to transmit or receive data with the mobile X-ray detector; and
at least one processor configured to:
control the communication interface to receive, from the mobile X-ray detector, imaging information of each of a plurality of X-ray images generated by the mobile X-ray detector and information about transmission, upon receiving the imaging information of each of the plurality of X-ray images and the information about transmission, transmit a first request signal for requesting a plurality of thumbnail images of the plurality of X-ray images to the mobile X-ray detector, and receive the plurality of thumbnail images from the mobile X-ray detector,
control the display to display the received plurality of thumbnail images on the display,
receive, through the user input interface, a user input for selecting one of the displayed plurality of thumbnail images,
control the communication interface to transmit, to the mobile X-ray detector, a second request signal for requesting to transmit a first X-ray image corresponding to the selected thumbnail image by the received user input, and
control the communication interface to receive, from the mobile X-ray detector, the first X-ray image.

17. The X-ray imaging apparatus of claim 16, wherein the at least one processor is further configured to:
detect the at least one non-transmitted X-ray image that is not transmitted or whose transmission is stopped from the mobile X-ray detector, and
control the display to display a user interface (UI) that requests to transmit the at least one non-transmitted X-ray image on the display.

18. The X-ray imaging apparatus of claim 16, wherein the at least one processor is further configured to:
receive, through the user input interface, a user input for instructing to delete an X-ray image from among the plurality of X-ray images displayed on the display,
obtain imaging information of the X-ray image selected by the received user input, and
control the communication interface to transmit obtained imaging information of the X-ray image, and
wherein the mobile X-ray detector is further configured to delete an X-ray image corresponding to the received imaging information from among at least one X-ray image stored in an external memory card of the mobile X-ray detector.

19. The X-ray imaging apparatus of claim 16, wherein the mobile X-ray detector is further configured to:
detect a storage capacity shortage of an external memory card, and
transmit, to the communication interface, a notification signal indicating the storage capacity shortage of the external memory card.

20. The X-ray imaging apparatus of claim 19, wherein the at least one processor is further configured to:
receive, through the user input interface, a user input for instructing to delete at least one X-ray image stored in the external memory card, and
control the communication interface to transmit, to the mobile X-ray detector, a third request signal for instructing to delete X-rag image,
wherein the mobile X-ray detector is further configured to delete the at least one X-ray image stored in the external memory card in response to the third request signal being received.

* * * * *